(12) United States Patent
von Geldern et al.

(10) Patent No.: US 11,827,596 B2
(45) Date of Patent: Nov. 28, 2023

(54) THYROMIMETICS

(71) Applicant: Autobahn Therapeutics, Inc., San Diego, CA (US)

(72) Inventors: Thomas von Geldern, Richmond, IL (US); Jean-Christophe Poupon, Shanghai (CN); Bradley Backes, San Francisco, CA (US)

(73) Assignee: AUTOBAHN THERAPEUTICS, INC., San Diego, CA (US)

(*) Notice: Subject to any disclaimer, the term of this patent is extended or adjusted under 35 U.S.C. 154(b) by 357 days.

(21) Appl. No.: 16/712,815

(22) Filed: Dec. 12, 2019

(65) Prior Publication Data

US 2020/0361849 A1    Nov. 19, 2020

Related U.S. Application Data

(60) Provisional application No. 62/907,455, filed on Sep. 27, 2019.

(30) Foreign Application Priority Data

Dec. 12, 2018  (WO) ................ PCT/CN2018/120634

(51) Int. Cl.
| | |
|---|---|
| C07C 69/157 | (2006.01) |
| A61P 5/14 | (2006.01) |
| C07C 233/11 | (2006.01) |
| C07C 57/36 | (2006.01) |

(52) U.S. Cl.
CPC .............. *C07C 69/157* (2013.01); *A61P 5/14* (2018.01); *C07C 57/36* (2013.01); *C07C 233/11* (2013.01)

(58) Field of Classification Search
CPC ...... C07C 69/157; C07C 57/36; C07C 233/11; A61P 5/14
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,652,441 A | 3/1987 | Okada et al. |
| 4,675,189 A | 6/1987 | Kent et al. |
| 4,677,191 A | 6/1987 | Tanaka et al. |
| 4,723,027 A | 2/1988 | Stoutamire et al. |
| 4,728,721 A | 3/1988 | Yamamoto et al. |
| 4,741,897 A | 5/1988 | Andrews et al. |
| 4,917,893 A | 4/1990 | Okada et al. |
| 4,992,445 A | 2/1991 | Lawter et al. |
| 5,001,139 A | 3/1991 | Lawter et al. |
| 5,023,252 A | 6/1991 | Hseih |
| 5,466,569 A | 11/1995 | Eber et al. |
| 5,616,345 A | 4/1997 | Geoghegan et al. |
| 5,883,294 A | 3/1999 | Scanlan et al. |
| 6,054,485 A | 4/2000 | Schwartz et al. |
| 6,107,517 A | 8/2000 | Scanlan et al. |
| 6,236,946 B1 | 5/2001 | Scanlan et al. |
| 7,288,571 B2 | 10/2007 | Hangeland et al. |
| 7,302,347 B2 | 11/2007 | Baxter et al. |
| 9,562,012 B2 | 2/2017 | Tanis et al. |
| 9,701,650 B2 | 7/2017 | Scanlan et al. |
| 10,130,643 B2 | 11/2018 | Cable et al. |
| 10,226,438 B2 | 3/2019 | Scanlan et al. |
| 10,392,356 B2 | 8/2019 | Scanlan et al. |
| 10,544,075 B2 | 1/2020 | Scanlan et al. |
| 10,870,616 B2 | 12/2020 | Scanlan et al. |
| 11,104,654 B2 | 8/2021 | Scanlan et al. |
| 11,325,886 B2 | 5/2022 | Scanlan et al. |
| 11,613,517 B2 | 3/2023 | Scanlan et al. |
| 2003/0203898 A1 | 10/2003 | Haning et al. |
| 2003/0215434 A1 | 11/2003 | Khan et al. |

(Continued)

FOREIGN PATENT DOCUMENTS

| | | |
|---|---|---|
| CN | 1882327 A | 12/2006 |
| CN | 101180097 A | 5/2008 |

(Continued)

OTHER PUBLICATIONS

Ashraf et al., Synthesis, characterization and in vitro hydrolysis studies of ester and amide prodrugs of dexibuprofen. Medicinal Chemistry Research 21:3361-3368 (2012).

(Continued)

*Primary Examiner* — Jeffrey S Lundgren
*Assistant Examiner* — William Y Lee
(74) *Attorney, Agent, or Firm* — WILSON SONSINI GOODRICH & ROSATI

(57) ABSTRACT

Compounds are provided having the structure of Formula (I):

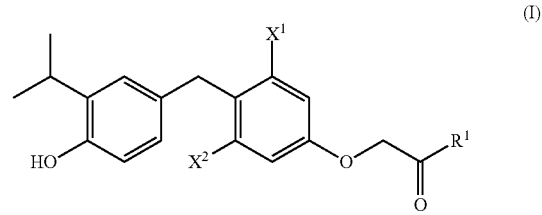

or a pharmaceutically acceptable isomer, racemate, hydrate, solvate, isotope, or salt thereof, wherein $X^1$, $X^2$, and $R^1$ are as defined herein. Such compounds function as thyromimetics and have utility for treating diseases such as neurodegenerative disorders and fibrotic diseases. Pharmaceutical compositions containing such compounds are also provided, as are methods of their use and preparation.

10 Claims, 2 Drawing Sheets

(56) References Cited

U.S. PATENT DOCUMENTS

| | | |
|---|---|---|
| 2005/0282872 A1 | 12/2005 | Hangeland et al. |
| 2007/0021407 A1 | 1/2007 | Boyle et al. |
| 2008/0124280 A1 | 5/2008 | Mousa et al. |
| 2008/0221170 A1 | 9/2008 | Roberts et al. |
| 2009/0028925 A1 | 1/2009 | Erion et al. |
| 2009/0062330 A1 | 3/2009 | Kalafer et al. |
| 2009/0105347 A1 | 4/2009 | Scanlan et al. |
| 2009/0232879 A1 | 9/2009 | Cable et al. |
| 2009/0306225 A1 | 12/2009 | Lichter et al. |
| 2009/0318514 A1 | 12/2009 | Garcia Collazo et al. |
| 2010/0099608 A1 | 4/2010 | Browning |
| 2010/0216771 A1 | 8/2010 | Li |
| 2010/0303934 A1 | 12/2010 | Soumyanath et al. |
| 2011/0178134 A1 | 7/2011 | Jaehne et al. |
| 2012/0004166 A1 | 1/2012 | Keil et al. |
| 2012/0245213 A1 | 9/2012 | Mosinger et al. |
| 2013/0289024 A1 | 10/2013 | Johansen et al. |
| 2014/0235676 A1 | 8/2014 | Landreth |
| 2014/0288077 A1 | 9/2014 | Fujii et al. |
| 2016/0081955 A1 | 3/2016 | Scanlan et al. |
| 2016/0244418 A1 | 8/2016 | Scanlan et al. |
| 2017/0007589 A1 | 1/2017 | Ding et al. |
| 2017/0226154 A1 | 8/2017 | Evans et al. |
| 2018/0057472 A1 | 3/2018 | Scanlan et al. |
| 2019/0175531 A1 | 6/2019 | Scanlan et al. |
| 2020/0181103 A1 | 6/2020 | Scanlan et al. |
| 2020/0405669 A1 | 12/2020 | Scanlan et al. |
| 2021/0002208 A1 | 1/2021 | Scanlan |
| 2021/0053917 A1 | 2/2021 | Von Geldern et al. |
| 2021/0087137 A1 | 3/2021 | Scanlan et al. |
| 2023/0048992 A1 | 2/2023 | Von Geldern et al. |

FOREIGN PATENT DOCUMENTS

| | | |
|---|---|---|
| CN | 101189248 A | 5/2008 |
| CN | 101547898 A | 9/2009 |
| CN | 101600450 A | 12/2009 |
| CN | 101610774 A | 12/2009 |
| CN | 101848712 A | 9/2010 |
| CN | 107848940 A | 3/2018 |
| EP | 3259246 A1 | 12/2017 |
| JP | 2004512303 A | 4/2004 |
| JP | 2004517037 A | 6/2004 |
| JP | 2008542301 A | 11/2008 |
| JP | 2008545711 A | 12/2008 |
| JP | 2012106996 A | 6/2012 |
| JP | 2016517884 A | 6/2016 |
| PE | 20180021 A1 | 1/2018 |
| RU | 2007148927 A | 7/2009 |
| WO | WO-9321146 A1 | 10/1993 |
| WO | WO-9900353 A1 | 1/1999 |
| WO | WO-0039077 A2 | 7/2000 |
| WO | WO-0073292 A1 | 12/2000 |
| WO | 01/60784 A1 | 8/2001 |
| WO | WO-02072539 A1 | 9/2002 |
| WO | WO-02081426 A1 | 10/2002 |
| WO | WO-2004043939 A1 | 5/2004 |
| WO | WO-2006031922 A2 | 3/2006 |
| WO | 2007/110226 A1 | 10/2007 |
| WO | WO-2008125724 A1 | 10/2008 |
| WO | WO-2013006734 A1 | 1/2013 |
| WO | WO-2014078892 A1 | 5/2014 |
| WO | WO-2014178892 A1 | 11/2014 |
| WO | WO-2014178931 A1 | 11/2014 |
| WO | WO-2015188015 A1 | 12/2015 |
| WO | WO-2016134292 A1 | 8/2016 |
| WO | WO-2017015360 A1 | 1/2017 |
| WO | 2017/201320 A1 | 11/2017 |
| WO | WO-2018032012 A1 | 2/2018 |
| WO | WO-2018208707 A1 | 11/2018 |
| WO | 2019/160980 A1 | 8/2019 |
| WO | WO-2020118564 A1 | 6/2020 |
| WO | WO-2020123861 A1 | 6/2020 |
| WO | WO-2020180624 A1 | 9/2020 |
| WO | WO-2021108549 A1 | 6/2021 |

OTHER PUBLICATIONS

Krogsgaard-Larsen et al. Chapter 4: Design and application of prodrugs. Textbook of Drug Designing and Discovery, US, Taylor & Francis Inc (3rd Ed.) (pp. P460-P514).

Martin et al. The proliferating cell nuclear antigen regulates retinoic acid receptor transcriptional activity through direct protein-protein interaction. Nucleic Acids Res. 33(13):4311-21 (2005).

PubChem SID 235918886 [https://pubchem.ncbi.nlm.nih.gov/substance/235918886] (2015).

Tegeli et al. Synthesis and evaluation of amide prodrugs of mefenamic acid. International Journal of Chemical Sciences 12(3):1033-1043.

Valadares et al. Role of halogen bonds in thyroid hormone receptor selectivity: pharmacophore-based 3D-QSSR studies. J Chem Inf Model 49(11):2606-2616 (2009).

Actis et al., Small molecule inhibitors of PCNA/PIP-box interaction suppress translesion DNA synthesis. Bioorg Med Chem. 21(7):1972-1977 (2013).

Alonso-Merino et al., Thyroid hormones inhibit TGF-beta signaling and attenuate fibrotic responses. Proc Natl Acad Sci U S A. 113(24):E3451-E3460 (2016).

Balkwill et al., Smoldering and polarized inflammation in the initiation and promotion of malignant disease. Cancer Cell 7(3):211-217 (2005).

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4):154-157 (2004).

Baxter et al., Selective modulation of thyroid hormone receptor action. J. Steroid Biochem. Mol. Bio. 76:31-42 (2001).

Berge et al. Pharmaceutical Salts. Journal of Pharmaceutical Sciences 66(1):1-19 (Jan. 1977).

Berkenstam et al., The thyroid hormone mimetic compound KB2115 lowers plasma LDL cholesterol and stimulates bile acid synthesis without cardiac effects in humans. Proc Natl Acad Sci U S A 105(2):663-667 (2008).

Bernal et al., Action of thyroid hormone in brain. J Endocrinol Invest. 25(3):268-288 (2002).

Bernal et al., Thyroid hormone receptors in brain development and function. Nat Clin Pract Endocrinol Metab. 3(3):249-259 (2007).

Biondi et al., Hypothyroidism as a risk factor for cardiovascular disease. Endocrine 24: 1-13 (2004).

Boger et al., Fatty acid amide hydrolase substrate specificity. Bioorg Med Chem Lett. 10(23):2613-2616 (2000).

Boymond et al., Preparation of highly functionalized grignard reagents by an iodine-magnesium exchange reaction and its application in solid-phase synthesis. Angew Chem Int Ed Engl. 37(12):1701-1703 (1998).

Calza et al., Thyroid hormone and remyelination in adult central nervous system: a lesson from an inflammatory-demyelinating disease. Brain Res Brain Res Rev. 48(2):339-346 (2005).

Chiellini et al., A high-affinity subtype-selective agonist ligand for the thyroid hormone receptor. Chemistry and Biology 5(6):299-306 (1998).

Chiellini et al., Synthesis and biological activity of novel thyroid hormone analogues: 5'-aryl substituted GC-1 derivatives. Bioorg Med Chem. 10(2):333-346 (2002).

Cravatt et al., Supersensitivity to anandamide and enhanced endogenous cannabinoid signaling in mice lacking fatty acid amide hydrolase. Proc Natl Acad Sci U S A 98(16):9371-9376 (2001).

Dell'Acqua et al., Functional and molecular evidence of myelin- and neuroprotection by thyroid hormone administration in experimental allergic encephalomyelitis. Neuropathol Appl Neurobiol. 38(5):454-470 (2012).

Devereaux et al., Increasing thyromimetic potency through halogen substitution. ChemMedChem. 11(21):2459-2465 (2016).

D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).

(56) References Cited

OTHER PUBLICATIONS

Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. Proc Natl Acad Sci U S A 104(39):15490-15495 (2007).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould et al. Salt Selection for Basic Drugs. Int J. Pharm. 33:201-217 (1986).
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
Johnson, Demyelinating diseases, in: The Infectious Etiology of Chronic Diseases: Defining the Relationship, Enhancing the Research, and Mitigating the Effects: Workshop Summary. Institute of Medicine (US) Forum on Microbial Threats; Knobler SL, O'Connor S, Lemon SM, et al., editors. Washington (DC): National Academies Press (US); 45-52 (2004).
Kavirajan et al., Efficacy and adverse effects of cholinesterase inhibitors and memantine in vascular dementia: a meta-analysis of randomised controlled trials. Lancet Neurol. 6(9):782-792 (2007).
Koenning et al., Myelin gene regulatory factor is required for maintenance of myelin and mature oligodendrocyte identity in the adult CNS. J Neurosci. 32(36):12528-12542 (2012).
Lee et al., Drug transporters in the central nervous system: brain barriers and brain parenchyma considerations. Pharmacological Review 53(4):569-596 (2001).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Malm et al., Recent advances in the development of agonists selective for beta1-type thyroid hormone receptor. Mini Rev Med Chem. 7(1):79-86 (2007).
Mandal et al., Pd-C-induced catalytic transfer hydrogenation with triethylsilane. Journal of Organic Chemistry 72(17):6599-6601 (2007).
Massague, J. TGFbeta signalling in context. Nat Rev Mol Cell Biol. 13(10):616-630 (2012).
Meinig et al., Targeting fatty-acid amide hydrolase with prodrugs for CNS-selective therapy. ACS Chem Neurosci. 8(11):2468-2476 (2017).
Miller et al., Primary-progressive multiple sclerosis. Lance Neurol. 6:903--912 (2007).
Miyabara et al., Thyroid hormone receptor-beta-selective agonist GC-24 spares skeletal muscle type I to II fiber shift. Cell Tissue Res. 321 (2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'Shea et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
PCT/CN2018/120634 International Search Report and Written Opinion dated Sep. 11, 2019.
PCT/US2019/066066 International Search Report and Written Opinion dated Mar. 5, 2020.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
Reichel et al., The role of blood-brain barrier studies in the pharmaceutical industry. Curr Drug Metab. 7(2):183-203 (2006).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term-Scanlan&rank=1).
Scanlan. Sobetirome: a case history of bench-to-clinic drug discovery and development. Heart Fail Rev 15:177-182 (2010).
Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).

(56) References Cited

OTHER PUBLICATIONS

Tangdenpaisal et al., Synthesis of the thyroid hormone analog GC-1 via Bi(OTf)3-catalyzed benzylation. Tetrahedron 70: 6789-6795 (2014).

Taub et al., Lipid lowering in healthy volunteers treated with multiple doses of MGL-3196, a liver-targeted thyroid hormone receptor-beta agonist. Atherosclerosis 230(2):373-380 (2013).

Trost et al., The thyroid hormone receptor-beta-selective agonist GC-1 differentially affects plasma lipids and cardiac activity. Endocrinology 141(9):3057-3064 (2000).

U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/ updated Mar. 1, 2021].

Varga et al., Antitransforming growth factor-beta therapy in fibrosis: recent progress and implications for systemic sclerosis. Curr Opin Rheumatol. 20(6):720-728 (2008).

Vattakatuchery et al., Acetylcholinesterase inhibitors in cognitive impairment in Huntington's disease: A brief review. 3(3):62-64 (2013).

Ye et al, Thyroid receptor ligands. 1. Agonist ligands selective for the thyroid receptor beta1. J Med Chem. 46(9):1580-1588 (2003).

Yen, P., Physiological and molecular basis of thyroid hormone action. Physiological Reviews 81(3):1097-1142 (2001).

Yoshihara et al., A designed antagonist of the thyroid hormone receptor. Bioorg Med Chem Lett. 11(21):2821-2825 (2001).

Yoshihara et al., Structural determinants of selective thyromimetics. J Med Chem. 46(14):3152-3161 (2003).

Zhang et al., Thyroid hormone potentially benefits multiple sclerosis via facilitating remyelination. Mol Neurobiol. 53(7):4406-4416 (2016).

Bastin et al. Salt selection and optimisation procedures for pharmaceutical new chemical entities. Organic Process Research & Development 4.5:427-435 (2000).

V. G. Belikov, "Pharmaceutical Chemistry: Manual", Moscow: MEDpress-inform, 2007, pp. 27-29.

Borngraeber et al. Ligand Selectivity by Seeking Hydrophobicity in Thyroid Hormone Receptor. PNAS USA 100(26):15358-15363 (2003).

Meinig et al., Structure-activity relationships of central nervous system penetration by fatty acid amide hydrolase (FAAH)-targeted thyromimetic prodrugs. ACS Med Chem Lett. 10(1):111-116 (2018).

Patani et al. Bioisosterism: A Rational Approach in Drug Design. Chem. Rev. 96:3147-3176 (1996).

PubChem SID 319635332 [ https://pubchem.ncbi.nlm.nih.gov/substance/319635332 ] (2016).

THYROMIMETICS

BACKGROUND

Technical Field

The invention relates to thyromimetic compounds and to products containing the same, as well as to methods of their use and preparation.

Description of the Related Art

Thyroid hormone (TH) is a key signal for oligodendrocyte differentiation and myelin formation during development, and also stimulates remyelination in adult models of multiple sclerosis (MS) (Calzà et al., Brain Res Revs 48:339-346, 2005). However, TH is not an acceptable long-term therapy due to the limited therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (TRs) (Malm et al., Mini Rev Med Chem 7:79-86, 2007). These receptors are expressed in two major forms with heterogenous tissue distributions and overlapping but distinct sets of target genes (Yen, Physiol Rev 81:1097-1142, 2001). TRα is enriched in the heart, brain, and bone while TRβ is enriched in the liver (O'Shea et al., Nucl Recept Signal 4:e011, 2006).

It has also been reported that TH can inhibit the transforming growth factor beta (TGF-β) signaling, and, therefore, attenuate fibrotic responses (Alonso-Merino et al., Proc Natl Acad Sci USA. 113(24):E3451-60, 2016). TGF-β is a cytokine with pleiotropic effects in tissue homeostasis that plays a key role in pathological processes such as fibrosis (Massagué, Nat Rev Mol Cell Biol. 13(10):616-630, 2012). By inhibiting TGF-β signalling, TR ligands or agonists could have beneficial effects to block the progression of fibrotic diseases, such as idiopathic pulmonary fibrosis (IPF) or systemic sclerosis (Varga et al., Curr Opin Rheumatol. 20(6): 720-728, 2008).

Developing selective thyromimetics has been challenging due to the high sequence homology of thyroid hormone receptor subtypes; namely, only one amino acid residue on the internal surface of the ligand binding domain cavity varies between the α1 and β1 forms. Despite this challenge, several groups have reported TRβ-selective agonists. Scanlan et al. identified GC-1 (sobetirome) as one of the first potent analogs to demonstrate significant TRP-selectivity in vitro (Chiellini et al., Chem Biol 5:299-306, 1998; Yoshihara et al., J Med Chem 46:3152-3161, 2003) and in vivo (Trost et al., Endocrinology 141:3057-3064, 2000; Grover et al., Endocrinology 145:1656-1661, 2004; Baxter et al., Trends Endocrinol Metab 15:154-157, 2004). As used herein, the term "sobetirome" refers to a synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1. Metabasis employs a similar core with a novel liver-targeting prodrug strategy in MB07811 (Erion et al., PNAS 104(39), 15490-15495, 2007). Madrigal has reported TRβ-selective activity in vivo for MGL-3196 (Taub et al., Atherosclerosis 230(2):373-380, 2013). KaroBio has reported on eprotirome (KB2115; Berkenstam et al., PNAS 105(2):663-668, 2008) and KB-141 (Ye et al., J Med Chem 46:1580-1588, 2003), both of which demonstrate improved TRP-selectivity in vitro. Further studies from this group highlight additional selective compounds (Hangeland et al., BMCL 14:3549-3553, 2004). Two TRβ-selective agonists, identified as SKL-12846 and SKL-13784, have been reported to accumulate in the liver and to reduce cholesterol levels in rodents (Takahashi et al., BMC 22(1):488-498, 2014; Xenobiotica 2015, 1-9). Kissei has also reported selective compounds (Shiohara et al., BMC 20(11), 3622-3634, 2012).

While progress has been made in this field, there remains a need in the art for further selective thyromimetic compounds, as well as to products containing the same, and for methods related to their use and preparation.

BRIEF SUMMARY

Disclosed herein are compounds according to Formula I:

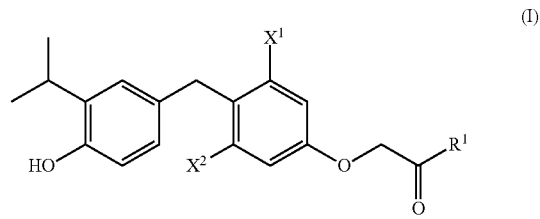

(I)

or a pharmaceutically acceptable isomer, racemate, hydrate, solvate, isotope, or salt thereof, wherein $X^1$, $X^2$, and $R^1$ are as defined below.

In an embodiment, a pharmaceutical composition is provided comprising a compound having the structure of Formula (I), or a pharmaceutically acceptable isomer, racemate, hydrate, solvate, isotope, or salt thereof, in combination with a pharmaceutically acceptable carrier, diluent, or excipient. In an embodiment, the pharmaceutical composition is for use in treating a neurodegenerative disorder including neurodegenerative disorders classified as a demyelinating disease such as X-linked adrenoleukodystrophy or multiple sclerosis. In another embodiment, the pharmaceutical composition is for use in treating a medical condition associated increased activity of TGF-3, such as a fibrotic disease.

In an embodiment, a method is provided for treating a neurodegenerative disorder in a subject in need thereof, comprising administering a compound having the structure of Formula (I), or a pharmaceutically acceptable salt or composition comprising the same. In some aspects, the neurodegenerative disorder can be classified as a demyelinating disease such as X-linked adrenoleukodystrophy or multiple sclerosis.

In another embodiment, a method is provided for treating a medical condition associated with over-expression of TGF-β in a subject in need thereof, comprising administering a compound having the structure of Formula (I), or a pharmaceutically acceptable salt or composition comprising the same. In some aspects, the medical condition associated with over-expression of TGF-β is a fibrotic disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
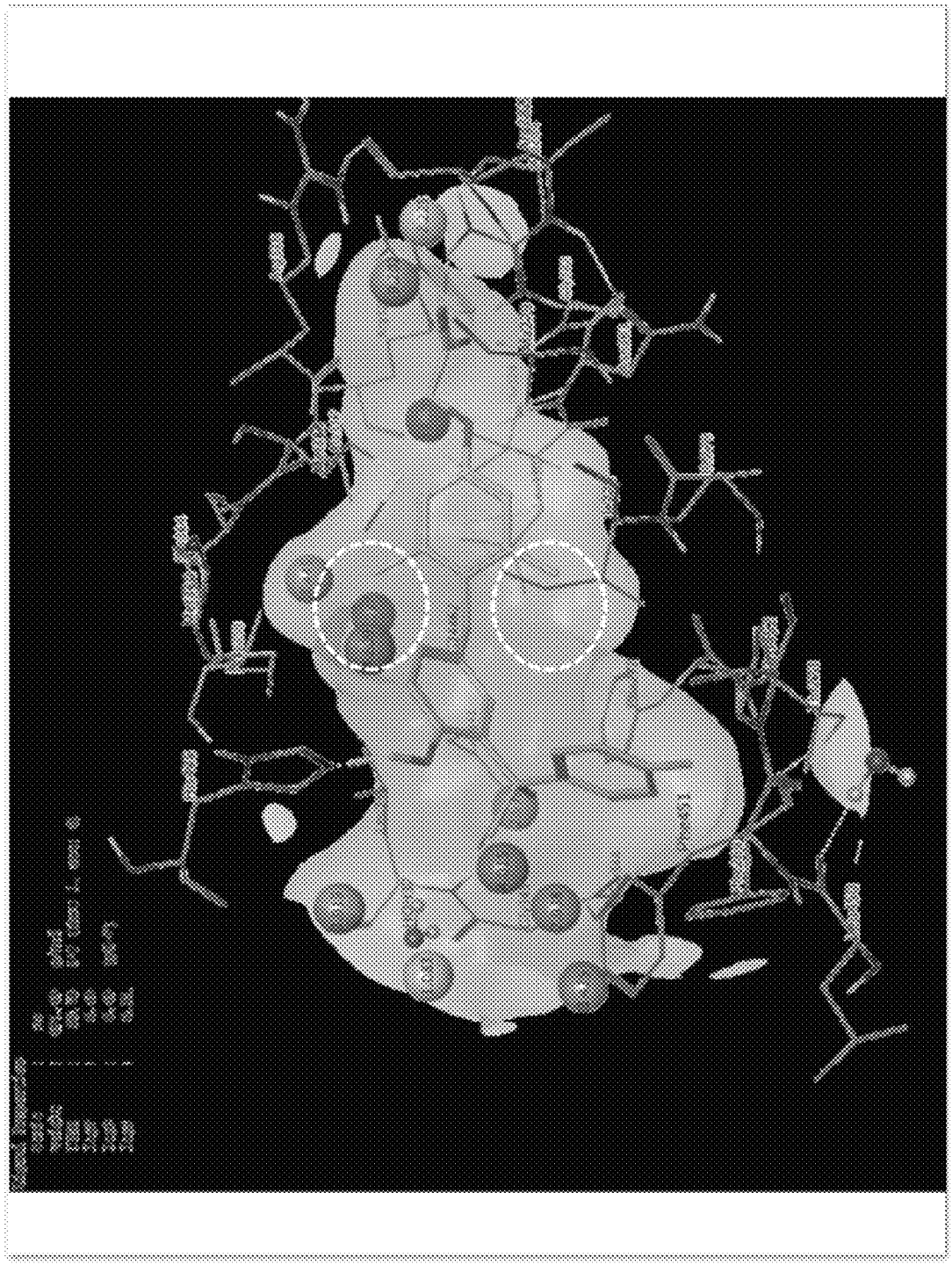
FIG. 1 depicts an X-ray crystal structure of sobetirome bound to the TRβ receptor (PDB 3IMY).

As mentioned above, the invention relates to thyromimetic compounds, to products comprising the same, and to methods for their use and synthesis.

In one embodiment, compounds are provided having the structure of Formula (I):

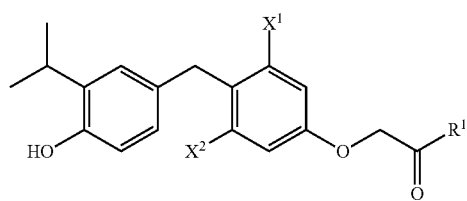

(I)

or a pharmaceutically acceptable isomer, racemate, hydrate, solvate, isotope, or salt thereof, wherein:

$X^1$ and $X^2$ are halo, lower alkyl, lower alkenyl, lower haloalkyl, lower alkoxy, lower haloalkoxy, cycloalkyl, and cycloalkylalkyl;
wherein
$X^1$ and $X^2$ do not have the same molecular formula, or
$X^1$ and $X^2$ have the same molecular formula, and $X^1$ and $X^2$ do not have the same connectivity or configuration;
$R^1$ is $-NR^{1a}R^{1b}$ or $-OR^{1c}$;
$R^{1a}$ and $R^{1b}$ are each, independently, H, $-OR^a$, $-NR^aR^b$, lower alkyl, lower alkenyl, lower alkynyl, carbocycle, carbocyclealkyl, heterocycle, or heterocyclealkyl, wherein $R^a$ and $R^b$ are each, independently, H or lower alkyl; and
$R^{1c}$ is H, lower alkyl, carbocycle, heterocycle, carbocyclealkyl, or heterocyclealkyl;
wherein $R^{1a}$, $R^{1b}$, $R^{1c}$, $R^a$, and $R^b$ are each, independently, optionally substituted with one or more halo, cyano, $-OR'$, $-NR'R''$, $-S(O)_2R'$ or $-S(O)_2OR'$, wherein $R'$ and $R''$ are each, independently, H or lower alkyl.

The acid compounds of the present invention ($R^1=-OR^{1c}$ and $R^{1c}=H$) are active agonists selectively activating the TRβ receptor. The amide compounds of the present invention ($R^1=-NR^{1a}R^{1b}$) may act as substrates for the specific hydrolase enzyme fatty acid-amide hydrolase (FAAH), which cleaves the amide, liberating the thyromimetic. Thus, prodrug conversion to drug is enhanced in tissues that express high levels of FAAH such as the central nervous system. The ester compounds of the present invention ($R^1=-OR^{1c}$ and $R^{1c} \neq H$) are also prodrugs, typically processed through the action of esterases which may exist selectively in specific tissues.

For compounds of the present invention, $X^1$ and $X^2$ do not have the same molecular formula, or if they do have the same molecular formula, they do not have the same connectivity or configuration. Examples where $X^1$ and $X^2$ do not have the same molecular formula include, but are not limited to, $X^1$ is methyl and $X^2$ is Cl, $X^1$ is $-CF_3$ and $X^2$ is methyl, $X^1$ is ethyl and $X^2$ is methyl, or $X^1$ is Br and $X^2$ is Cl. Examples where $X^1$ and $X^2$ have the same molecular formula, but not the same connectivity include, but are not limited to, $X^1$ is propyl and $X^2$ is isopropyl, or $X^1$ is propenyl and $X^2$ is cyclopropyl. Examples where $X^1$ and $X^2$ have the same molecular formula, but not the same configuration include, but are not limited to, $X^1$ is (Z)

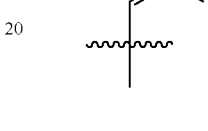

and $X^2$ is (E)

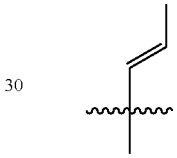

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of straight chain lower alkyl groups include, but are not limited to, methyl, ethyl, n-propyl, n-butyl, n-pentyl-, n-hexyl, n-heptyl, and n-octyl groups. Examples of branched lower alkyl groups include, but are not limited to, isopropyl, isobutyl, sec-butyl, t-butyl, neopentyl, isopentyl, and 2,2-dimethylpropyl groups.

As used herein, "lower alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, isopropenyl, butenyl, pentenyl, and hexenyl.

As used herein, "lower alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of lower alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to $-OH$.

"Cyano" refers to $-CN$.

"Lower haloalkyl" refers to a lower alkyl as defined above with one or more hydrogen atoms replaced with halogen. Examples of lower haloalkyl groups include, but are not limited to, —$CF_3$, —$CHF_2$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, isopropoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, —$OCF_3$, —$OCHF_2$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups may also be optionally substituted, including, but not limited to, alkyl, halo, amino, hydroxy, cyano, carboxy, nitro, thio, or alkoxy groups bonded to one of the cycloalkyl ring members.

"Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like). In one embodiment, aryl is phenyl or naphthyl, and in another embodiment aryl is phenyl. Aryl groups may also be optionally substituted, including, but not limited to, alkyl, halo, amino, hydroxy, cyano, carboxy, nitro, thio, or alkoxy groups bonded to one of the aryl ring members.

"Carbocyclyl," "carbocycle," or "carbocyclic" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above. Carbocyclyl groups may also be optionally substituted, including, but not limited to, alkyl, halo, amino, hydroxy, cyano, carboxy, nitro, thio, or alkoxy groups bonded to one of the carbocyclyl ring members.

"Carbocyclealkyl" are alkyl groups as defined above in which a hydrogen or carbon bond of the alkyl group is replaced with a bond to a carbocycle group as defined above.

"Heterocyclyl," "heterocycle," or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzodioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl. Heterocyclyl groups may also be optionally substituted, including, but not limited to, alkyl, halo, amino, hydroxy, cyano, carboxy, nitro, thio, or alkoxy groups bonded to one of the heterocyclyl ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclealkyl" are alkyl groups as defined above in which a hydrogen or carbon bond of the alkyl group is replaced with a bond to a heterocycle group as defined above.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. Heteroaryl groups may also be optionally substituted, including, but not limited to, alkyl, halo, amino, hydroxy, cyano, carboxy, nitro, thio, or alkoxy groups bonded to one of the heteroaryl ring members.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include —F, —Cl, —Br, —I, —OR, —OC(O)N(R)$_2$, —CN, —$CF_3$, —$OCF_3$, R, =O, =S, —C(O)—, —S(O)—, methylenedioxy, ethylenedioxy, —N(R)$_2$, —SR, —S(O)R, —S(O)$_2$R, —S(O)$_2$N(R)$_2$, —S(O)$_2$OR, —C(O)R, —C(O)C(O)R, —C(O)CH$_2$C(O)R, —C(S)R, —C(O)OR, —OC(O)R, —C(O)N(R)$_2$, —OC(O)N(R)$_2$, —C(S)N(R)$_2$, —(CH$_2$)$_{0-2}$NHC(O)R, —(CH$_2$)$_{0-2}$N(R)N(R)$_2$, —N(R)N(R)C(O)R, —N(R)N(R)C(O)OR, —N(R)N(R)C(O)N(R)$_2$, —N(R)S(O)$_2$R, —N(R)S(O)$_2$N(R)$_2$, —N(R)C(O)OR, —N(R)C(O)R, —N(R)C(S)R, —N(R)C(O)N(R)$_2$, —N(R)C(S)N(R)$_2$, —N(COR)COR, —N(OR)R, —C(=NH)N(R)$_2$, —C(O)N(OR)R, or —C(=NOR)R wherein R can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles. The substituents of the substituted groups can further be substituted with alkyl, alkenyl, cycloalkyl, aryl, heteroaryl, and alkynyl groups as defined herein, which can themselves be further substituted. For example, a $C_{1-4}$ alkyl group can be substituted with an amide, and the amide can further be substituted with another $C_{1-4}$ alkyl, which can further be substituted.

Substituted ring groups such as substituted carbocylyl, aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

In one embodiment, compounds are provided having the structure of Formula (II):

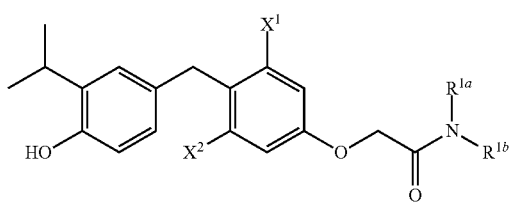

(II)

or a pharmaceutically acceptable isomer, racemate, hydrate, solvate, isotope, or salt thereof, wherein:
$X^1$ and $X^2$ are halo, lower alkyl, lower alkenyl, lower haloalkyl, lower alkoxy, lower haloalkoxy, cycloalkyl, and cycloalkylalkyl;
wherein
$X^1$ and $X^2$ do not have the same molecular formula, or
$X^1$ and $X^2$ have the same molecular formula, and $X^1$ and $X^2$ do not have the same connectivity or configuration; and
$R^{1a}$ and $R^{1b}$ are each, independently, H, —OR$^a$, —NR$^a$R$^b$, lower alkyl, lower alkenyl, lower alkynyl, carbocycle, carbocyclealkyl, heterocycle, or heterocyclealkyl;
wherein R$^a$ and R$^b$ are each, independently, H or lower alkyl; and
wherein $R^{1a}$, $R^{1b}$, R$^a$, and R$^b$ are each, independently, optionally substituted with one or more halo, cyano, —OR', —NR'R", —S(O)$_2$R' or —S(O)$_2$OR', wherein R' and R" are each, independently, H or lower alkyl.

In one embodiment, compounds are provided having the structure of Formula (III):

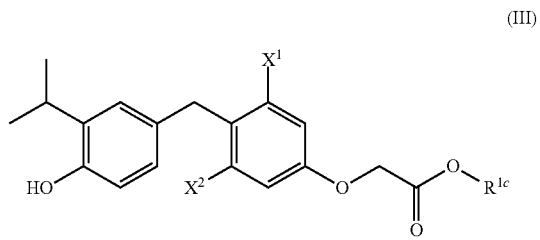

(III)

or a pharmaceutically acceptable isomer, racemate, hydrate, solvate, isotope, or salt thereof, wherein:
$X^1$ and $X^2$ are halo, lower alkyl, lower alkenyl, lower haloalkyl, lower alkoxy, lower haloalkoxy, cycloalkyl, and cycloalkylalkyl;
wherein
$X^1$ and $X^2$ do not have the same molecular formula, or
$X^1$ and $X^2$ have the same molecular formula, and $X^1$ and $X^2$ do not have the same connectivity or configuration; and
$R^{1c}$ is H, lower alkyl, carbocycle, heterocycle, carbocyclealkyl, or heterocyclealkyl, wherein $R^{1c}$ is optionally substituted with one or more halo, cyano, —OR, —NR'R", —S(O)$_2$R' or —S(O)$_2$OR', wherein R' and R" are each, independently, H or lower alkyl.

In one embodiment, compounds are provided having the structure of Formula (IV):

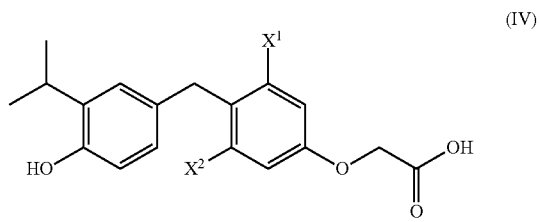

(IV)

or a pharmaceutically acceptable isomer, racemate, hydrate, solvate, isotope, or salt thereof, wherein:
$X^1$ and $X^2$ are halo, lower alkyl, lower alkenyl, lower haloalkyl, lower alkoxy, lower haloalkoxy, cycloalkyl, and cycloalkylalkyl;
wherein
$X^1$ and $X^2$ do not have the same molecular formula, or
$X^1$ and $X^2$ have the same molecular formula, and $X^1$ and $X^2$ do not have the same connectivity or configuration.

In one embodiment, compounds having the structure of Formulas (I) or (II) are provided, or a pharmaceutically acceptable isomer, racemate, hydrate, solvate, isotope, or salt thereof, wherein $R^{1a}$ is H.

In one embodiment, compounds having the structure of Formulas (I) or (II) are provided, or a pharmaceutically acceptable isomer, racemate, hydrate, solvate, isotope, or salt thereof, wherein $R^{1a}$ is lower alkyl. In another embodiment, $R^{1a}$ is methyl.

In one embodiment, compounds having the structure of Formulas (I) or (II) are provided, or a pharmaceutically acceptable isomer, racemate, hydrate, solvate, isotope, or salt thereof, wherein $R^{1b}$ is H.

In one embodiment, compounds having the structure of Formulas (I) or (II) are provided, or a pharmaceutically acceptable isomer, racemate, hydrate, solvate, isotope, or salt thereof, wherein $R^{1b}$ is lower alkyl. In another embodiment, $R^{1b}$ is methyl.

In one embodiment, compounds having the structure of Formulas (I) or (II) are provided, or a pharmaceutically acceptable isomer, racemate, hydrate, solvate, isotope, or salt thereof, wherein $R^{1a}$ is lower alkyl and $R^{1b}$ is H. In another embodiment, $R^{1a}$ is methyl and $R^{1b}$ is H.

In one embodiment, compounds having the structure of Formulas (I) or (II) are provided, or a pharmaceutically acceptable isomer, racemate, hydrate, solvate, isotope, or salt thereof, wherein $R^{1a}$ is lower alkyl and $R^{1b}$ is lower alkyl. In another embodiment, $R^{1a}$ is methyl and $R^{1b}$ is methyl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl. In one embodiment, $R^{1c}$ is methyl or ethyl. In one embodiment, $R^{1c}$ is methyl. In another embodiment, $R^{1c}$ is ethyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower alkyl. In one embodiment, $X^1$ is methyl, ethyl, propyl, or isopropyl. In one embodiment, $X^1$ is methyl. In one embodiment, $X^1$ is ethyl. In one embodiment, $X^1$ is propyl. In another embodiment, $X^1$ is isopropyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower alkenyl. In one embodiment, $X^1$ is ethenyl, propenyl, or isopropenyl. In one embodiment $X^1$ is ethenyl. In one embodiment, $X^1$ is propenyl. In one embodiment, $X^1$ is

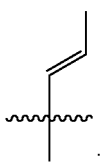

In another embodiment, $X^1$ is isopropenyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is cycloalkyl. In another embodiment, $X^1$ is cyclopropyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower haloalkyl. In another embodiment, $X^1$ is trifluoromethyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is halo. In one embodiment, $X^1$ is Cl or Br. In one embodiment, $X^1$ is Cl. In another embodiment, $X^1$ is Br.

In one embodiment, compounds having the structure of Formulas (I), (II), (III), or (IV) are provided, or a pharmaceutically acceptable isomer, racemate, hydrate, solvate, isotope, or salt thereof, wherein $X^2$ is halo. In one embodiment, $X^2$ is Cl or Br. In one embodiment, $X^2$ is Cl. In another embodiment, $X^2$ is Br.

In one embodiment, compounds having the structure of Formulas (I), (II), (III), or (IV) are provided, or a pharmaceutically acceptable isomer, racemate, hydrate, solvate, isotope, or salt thereof, wherein $X^2$ is lower alkyl. In another embodiment, $X^2$ is methyl.

In one embodiment, compounds having the structure of Formulas (I) or (II) are provided, or a pharmaceutically acceptable isomer, racemate, hydrate, solvate, isotope, or salt thereof, wherein $R^{1a}$ is lower alkyl, $R^{1b}$ is H, $X^1$ is lower alkyl, and $X^2$ is halo. In one embodiment, $R^{1a}$ is methyl, $R^{1b}$ is H, $X^1$ is methyl, and $X^2$ is Cl. In another embodiment, $R^{1a}$ is methyl, $R^{1b}$ is H, $X^1$ is methyl, and $X^2$ is Br.

In one embodiment, compounds having the structure of Formulas (I) or (II) are provided, or a pharmaceutically acceptable isomer, racemate, hydrate, solvate, isotope, or salt thereof, wherein $R^{1a}$ is lower alkyl, $R^{1b}$ is lower alkyl, $X^1$ is lower alkyl, and $X^2$ is halo. In another embodiment, $R^{1a}$ is methyl, $R^{1b}$ is methyl, $X^1$ is ethyl, and $X^2$ is Cl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is lower alkyl, and $X^2$ is halo. In one embodiment, $R^{1c}$ is methyl, $X^1$ is methyl, and $X^2$ is Cl. In one embodiment, $R^{1c}$ is methyl, $X^1$ is methyl, and $X^2$ is Br. In another embodiment, $R^{1c}$ is ethyl, $X^1$ is ethyl, and $X^2$ is Cl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is halo, and $X^2$ is halo. In another embodiment, $R^{1c}$ is ethyl, $X^1$ is Br, and $X^2$ is Cl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is lower alkyl, and $X^2$ is lower alkyl. In one embodiment, $R^{1c}$ is ethyl, $X^1$ is ethyl, and $X^2$ is methyl. In another embodiment, $R^{1c}$ is ethyl, $X^1$ is propyl, and $X^2$ is methyl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is lower alkenyl, and $X^2$ is lower alkyl. In one embodiment, $R^{1c}$ is ethyl, $X^1$ is ethenyl, and $X^2$ is methyl. In one embodiment, $R^{1c}$ is ethyl, $X^1$ is propenyl, and $X^2$ is methyl. In one embodiment, $R^{1c}$ is ethyl, $X^1$ is

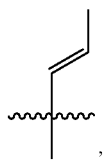 [SMILES: */C=C/C]

and $X^2$ is methyl. In another embodiment, $R^{1c}$ is ethyl, $X^1$ is isopropenyl, and $X^2$ is methyl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is lower alkenyl, and $X^2$ is halo. In another embodiment, $R^{1c}$ is ethyl, $X^1$ is isopropenyl, and $X^2$ is Cl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is halo, and $X^2$ is lower alkyl. In another embodiment, $R^{1c}$ is ethyl, $X^1$ is Br, and $X^2$ is methyl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is lower haloalkyl, and $X^2$ is lower alkyl. In another embodiment, $R^{1c}$ is ethyl, $X^1$ is trifluoromethyl, and $X^2$ is methyl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is lower haloalkyl, and $X^2$ is halo. In another embodiment, $R^{1c}$ is ethyl, $X^1$ is trifluoromethyl, and $X^2$ is Cl.

In one embodiment, compounds having the structure of Formulas (I) or (III) are provided, or a pharmaceutically acceptable isomer, racemate, hydrate, solvate, isotope, or salt thereof, wherein $R^{1c}$ is lower alkyl, $X^1$ is cycloalkyl, and $X^2$ is lower alkyl. In another embodiment, $R^{1c}$ is ethyl, $X^1$ is cyclopropyl, and $X^2$ is methyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower alkyl and $X^2$ is halo. In one embodiment, $X^1$ is methyl and $X^2$ is Cl or Br. In one embodiment, $X^1$ is ethyl and $X^2$ is Cl or Br. In one embodiment, $X^1$ is isopropyl and $X^2$ is Cl or Br. In one embodiment, $X^1$ is methyl and $X^2$ is Cl. In one embodiment, $X^1$ is methyl and $X^2$ is Br. In one embodiment, $X^1$ is ethyl and $X^2$ is Cl. In one embodiment, $X^1$ is ethyl and $X^2$ is Br. In one embodiment, $X^1$ is isopropyl and $X^2$ is Cl. In another embodiment, $X^1$ is isopropyl and $X^2$ is Br.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower alkyl, and $X^2$ is lower alkyl. In one embodiment, $X^1$ is ethyl and $X^2$ is methyl. In one embodiment, $X^1$ is propyl and $X^2$ is methyl. In another embodiment, $X^1$ is isopropyl and $X^2$ is methyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower haloalkyl, and $X^2$ is lower alkyl. In another embodiment, $X^1$ is trifluoromethyl and $X^2$ is methyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower haloalkyl, and $X^2$ is halo. In another embodiment, $X^1$ is trifluoromethyl and $X^2$ is Cl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower alkenyl, and $X^2$ is lower alkyl. In one embodiment, $X^1$ is ethenyl and $X^2$ is methyl. In one embodiment, $X^1$ is propenyl and $X^2$ is methyl. In one embodiment, $X^1$ is

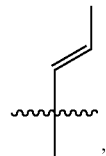 [SMILES: */C=C/C]

and $X^2$ is methyl. In another embodiment, $X^1$ is isopropenyl and $X^2$ is methyl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is lower alkenyl, and $X^2$ is halo. In another embodiment, $X^1$ is isopropenyl and $X^2$ is Cl.

In one embodiment, compounds having the structure of Formulas (I), (II), (III), or (IV) are provided, or a pharmaceutically acceptable isomer, racemate, hydrate, solvate, isotope, or salt thereof, wherein $X^1$ is cycloalkyl, and $X^2$ is lower alkyl. In another embodiment, $X^1$ is cyclopropyl and $X^2$ is methyl.

Representative compounds of Formula (I), and Formulas (II) through (IV) as applicable, include the compounds listed in Table 1 below, as well as pharmaceutically acceptable salts thereof. To this end, representative compounds are identified herein by their respective "Compound Number", which is sometimes abbreviated as "Compound No.", "Cmpd. No." or "No."

TABLE 1

Representative Compounds

| Cmpd. No. | Structure | Name |
|---|---|---|
| 1 | 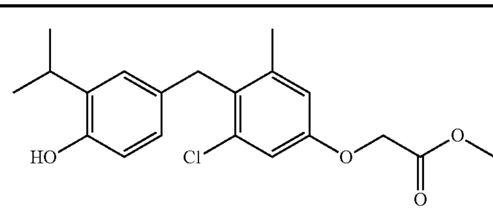 | methyl 2-(3-chloro-4-(4-hydroxy-3-isopropylbenzyl)-5-methylphenoxy)acetate |

TABLE 1-continued

Representative Compounds

| Cmpd. No. | Structure | Name |
|---|---|---|
| 2 | 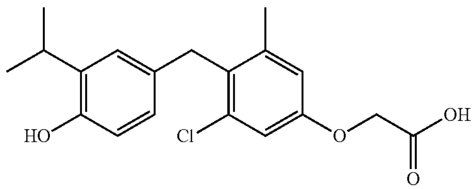 [SMILES: Cc1cc(OCC(=O)O)cc(Cl)c1Cc1ccc(O)c(C(C)C)c1] | 2-(3-chloro-4-(4-hydroxy-3-isopropylbenzyl)-5-methylphenoxy)acetic acid |
| 3 | 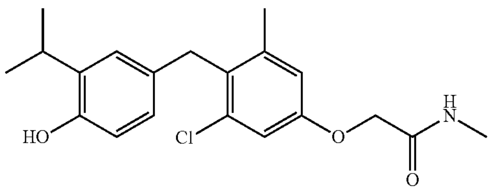 [SMILES: CNC(=O)COc1cc(C)c(Cc2ccc(O)c(C(C)C)c2)c(Cl)c1] | 2-(3-chloro-4-(4-hydroxy-3-isopropylbenzyl)-5-methylphenoxy)-N-methylacetamide |
| 4 | 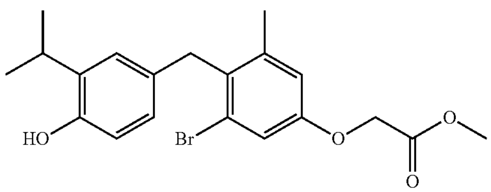 | methyl 2-(3-bromo-4-(4-hydroxy-3-isopropylbenzyl)-5-methylphenoxy)acetate |
| 5 | 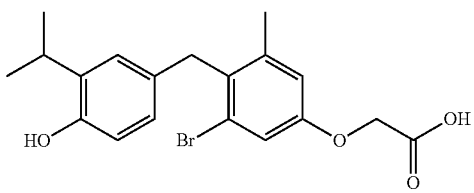 [SMILES: Cc1cc(OCC(=O)O)cc(Br)c1Cc1ccc(O)c(C(C)C)c1] | 2-(3-bromo-4-(4-hydroxy-3-isopropylbenzyl)-5-methylphenoxy)acetic acid |
| 6 | 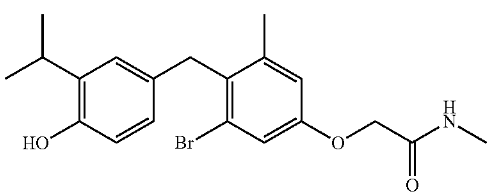 [SMILES: CNC(=O)COc1cc(C)c(Cc2ccc(O)c(C(C)C)c2)c(Br)c1] | 2-(3-bromo-4-(4-hydroxy-3-isopropylbenzyl)-5-methylphenoxy)-N-methylacetamide |
| 7 | 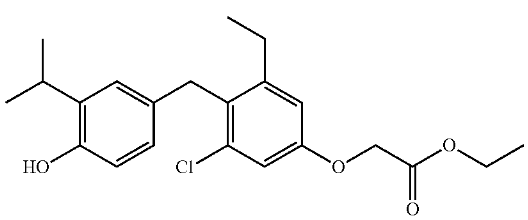 [SMILES: CCOC(=O)COc1cc(Cl)c(Cc2ccc(O)c(C(C)C)c2)c(CC)c1] | ethyl 2-(3-chloro-5-ethyl-4-(4-hydroxy-3-isopropylbenzyl)phenoxy)acetate |
| 8 | 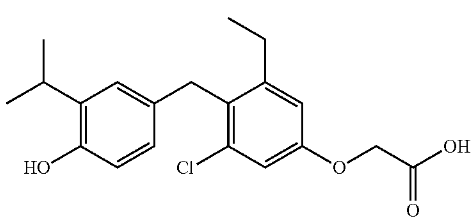 [SMILES: CCc1cc(OCC(=O)O)cc(Cl)c1Cc1ccc(O)c(C(C)C)c1] | 2-(3-chloro-5-ethyl-4-(4-hydroxy-3-isopropylbenzyl)phenoxy)acetic acid |

TABLE 1-continued

Representative Compounds

| Cmpd. No. | Structure | Name |
|---|---|---|
| 9 | 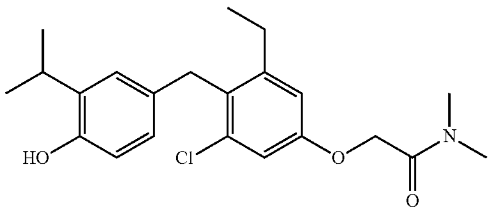 [SMILES: CCc1cc(OCC(=O)N(C)C)cc(Cl)c1Cc1ccc(O)c(C(C)C)c1] | 2-(3-chloro-5-ethyl-4-(4-hyroxy-3-isopropylbenzyl)phenoxy)-N,N-dimethylacetamide |
| 10 | 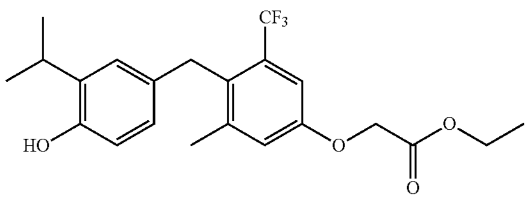 [SMILES: CCOC(=O)COc1cc(C)c(Cc2ccc(O)c(C(C)C)c2)c(C(F)(F)F)c1] | ethyl 2-(4-(4-hydroxy-3-isopropylbenzyl)-3-methyl-5-(trifluoromethyl)phenoxy)acetate |
| 11 | 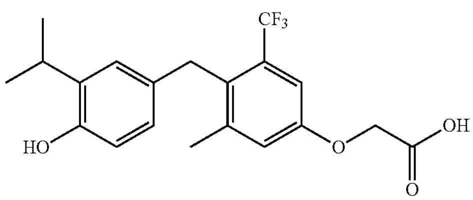 [SMILES: Cc1cc(OCC(=O)O)cc(C(F)(F)F)c1Cc1ccc(O)c(C(C)C)c1] | 2-(4-(4-hydroxy-3-isopropylbenzyl)-3-methyl-5-(trifluoromethyl)phenoxy)acetic acid |
| 12 | 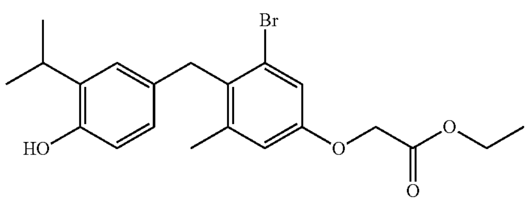 [SMILES: CCOC(=O)COc1cc(C)c(Cc2ccc(O)c(C(C)C)c2)c(Br)c1] | ethyl 2-(3-bromo-4-(4-hydroxy-3-isopropylbenzyl)-5-methylphenoxy)acetate |
| 13 | 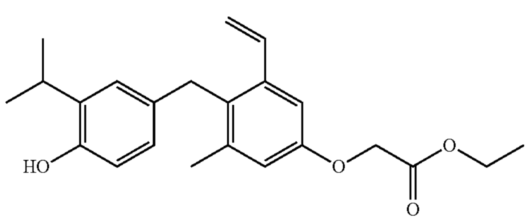 [SMILES: C=Cc1cc(OCC(=O)OCC)cc(C)c1Cc1ccc(O)c(C(C)C)c1] | ethyl 2-(4-(4-hydroxy-3-isopropylbenzyl)-3-methyl-5-vinylphenoxy)acetate |
| 14 | 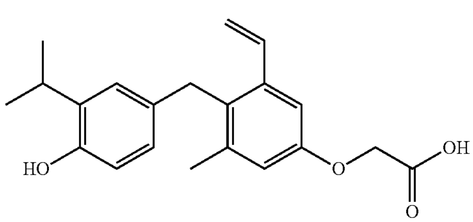 [SMILES: C=Cc1cc(OCC(=O)O)cc(C)c1Cc1ccc(O)c(C(C)C)c1] | 2-(4-(4-hydroxy-3-isopropylbenzyl)-3-methyl-5-vinylphenoxy)acetic acid |
| 15 | 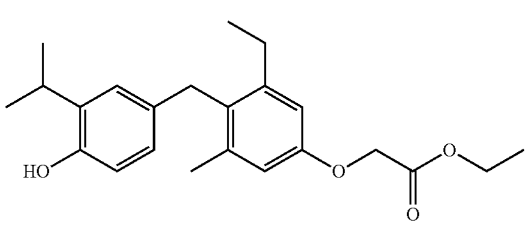 [SMILES: CCOC(=O)COc1cc(C)c(Cc2ccc(O)c(C(C)C)c2)c(CC)c1] | ethyl 2-(3-ethyl-4-(4-hydroxy-3-isopropylbenzyl)-5-methylphenoxy)acetate |

TABLE 1-continued

Representative Compounds

| Cmpd. No. | Structure | Name |
|---|---|---|
| 16 | 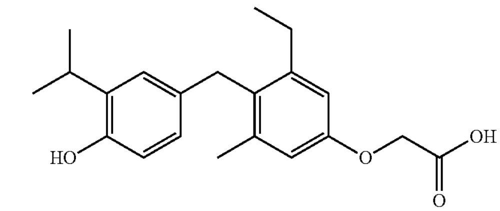 [SMILES: CCc1cc(OCC(=O)O)cc(C)c1Cc1ccc(O)c(C(C)C)c1] | 2-(3-ethyl-4-(4-hydroxy-3-isopropylbenzyl)-5-methylphenoxy)acetic acid |
| 17 | 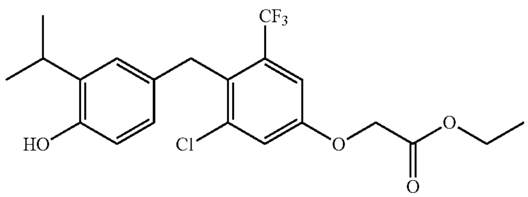 [SMILES: CCOC(=O)COc1cc(Cl)c(Cc2ccc(O)c(C(C)C)c2)c(C(F)(F)F)c1] | ethyl 2-(3-chloro-4-(4-hydroxy-3-isopropylbenzyl)-5-(trifluoromethyl)phenoxy)acetate |
| 18 | 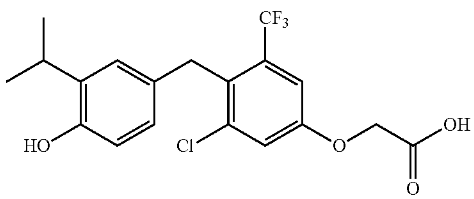 [SMILES: CC(C)c1cc(Cc2c(Cl)cc(OCC(=O)O)cc2C(F)(F)F)ccc1O] | 2-(3-chloro-4-(4-hydroxy-3-isopropylbenzyl)-5-(trifluoromethyl)phenoxy)acetic acid |
| 19 | 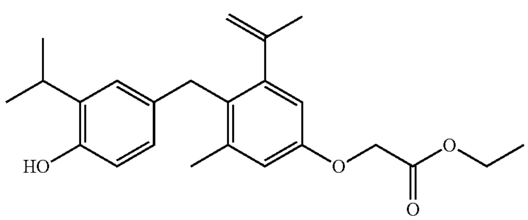 [SMILES: C=C(C)c1cc(OCC(=O)OCC)cc(C)c1Cc1ccc(O)c(C(C)C)c1] | ethyl 2-(4-(4-hydroxy-3-isopropylbenzyl)-3-methyl-5-(prop-1-en-2-yl)phenoxy)acetate |
| 20 | 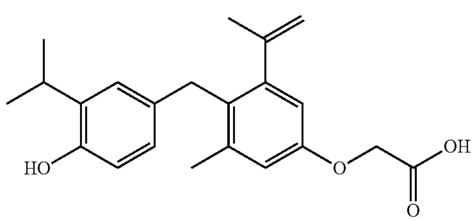 [SMILES: C=C(C)c1cc(OCC(=O)O)cc(C)c1Cc1ccc(O)c(C(C)C)c1] | 2-(4-(4-hydroxy-3-isopropylbenzyl)-3-methyl-5-(prop-1-en-2-yl)phenoxy)acetic acid |
| 21 | 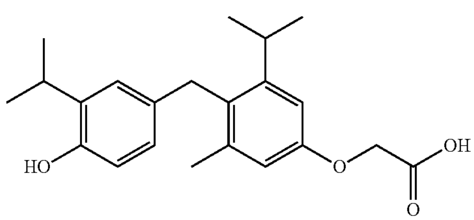 [SMILES: Cc1cc(OCC(=O)O)cc(C(C)C)c1Cc1ccc(O)c(C(C)C)c1] | 2-(4-(4-hydroxy-3-isopropylbenzyl)-3-isopropyl-5-methylphenoxy)acetic acid |
| 22 | 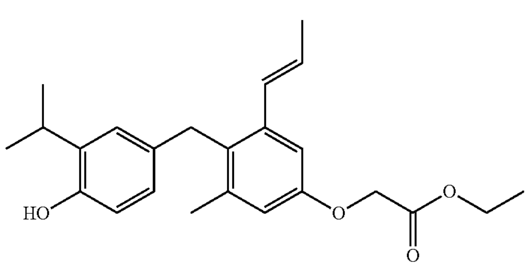 [SMILES: C/C=C/c1cc(OCC(=O)OCC)cc(C)c1Cc1ccc(O)c(C(C)C)c1] | (E)-ethyl 2-(4-(4-hydroxy-3-isopropylbenzyl)-3-methyl-5-(prop-1-enyl)phenoxy)acetate |

TABLE 1-continued

Representative Compounds

| Cmpd. No. | Structure | Name |
|---|---|---|
| 23 | 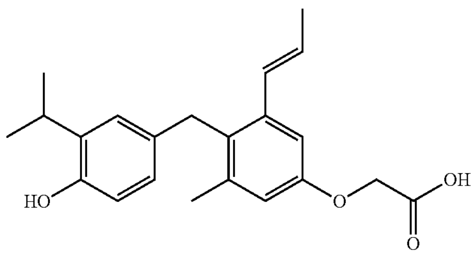 [SMILES: C/C=C/c1cc(OCC(=O)O)cc(C)c1Cc1ccc(O)c(C(C)C)c1] | (E)-2-(4-(4-hydroxy-3-isopropylbenzyl)-3-methyl-5-(prop-1-enyl)phenoxy)acetic acid |
| 24 | 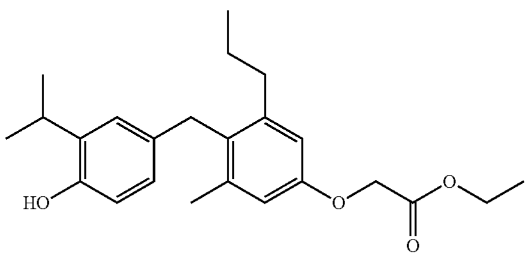 [SMILES: CCCc1cc(OCC(=O)OCC)cc(C)c1Cc1ccc(O)c(C(C)C)c1] | ethyl 2-(4-(4-hydroxy-3-isopropylbenzyl)-3-methyl-5-propylphenoxy)acetate |
| 25 | 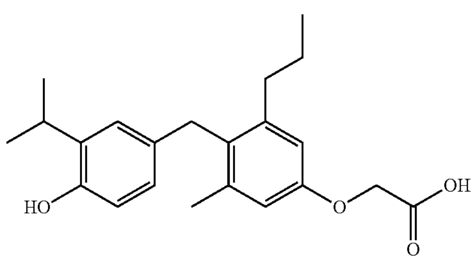 [SMILES: CCCc1cc(OCC(=O)O)cc(C)c1Cc1ccc(O)c(C(C)C)c1] | 2-(4-(4-hydroxy-3-isopropylbenzyl)-3-methyl-5-propylphenoxy)acetic acid |
| 26 | 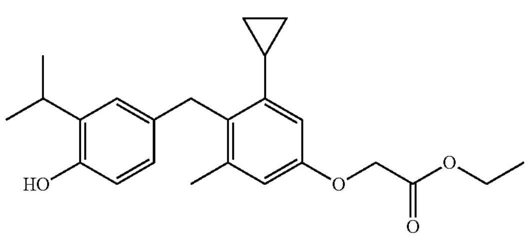 [SMILES: CCOC(=O)COc1cc(C)c(Cc2ccc(O)c(C(C)C)c2)c(C2CC2)c1] | ethyl 2-(3-cyclopropyl-4-(4-hydroxy-3-isopropylbenzyl)-5-methylphenoxy)acetate |
| 27 | 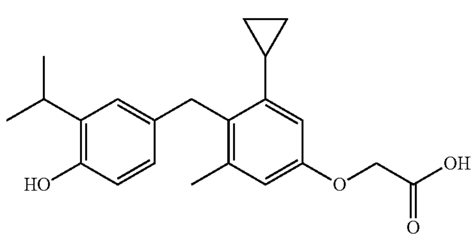 [SMILES: Cc1cc(OCC(=O)O)cc(C2CC2)c1Cc1ccc(O)c(C(C)C)c1] | 2-(3-cyclopropyl-4-(4-hydroxy-3-isopropylbenzyl)-5-methylphenoxy)acetic acid |
| 28 | 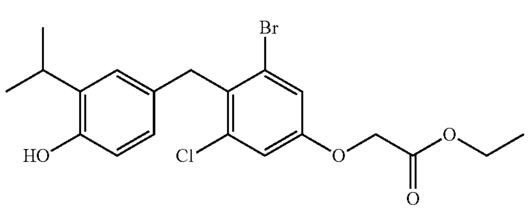 [SMILES: CCOC(=O)COc1cc(Cl)c(Cc2ccc(O)c(C(C)C)c2)c(Br)c1] | ethyl 2-(3-bromo-5-chloro-4-(4-hydroxy-3-isopropylbenzyl)phenoxy)acetate |

TABLE 1-continued

Representative Compounds

| Cmpd. No. | Structure | Name |
|---|---|---|
| 29 | 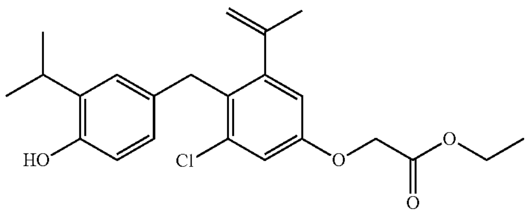 [SMILES: C=C(C)c1cc(OCC(=O)OCC)cc(Cl)c1Cc1ccc(O)c(C(C)C)c1] | ethyl 2-(3-chloro-4-(4-hydroxy-3-isopropylbenzyl)-5-(prop-1-en-2-yl)phenoxy)acetate |
| 30 | 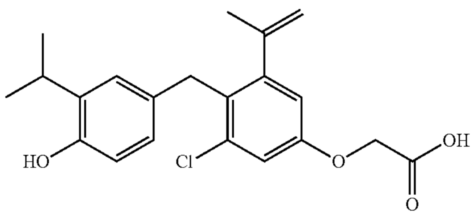 [SMILES: C=C(C)c1cc(OCC(=O)O)cc(Cl)c1Cc1ccc(O)c(C(C)C)c1] | 2-(3-chloro-4-(4-hydroxy-3-isopropylbenzyl)-5-(prop-1-en-2-yl)phenoxy)acetic acid |
| 31 | 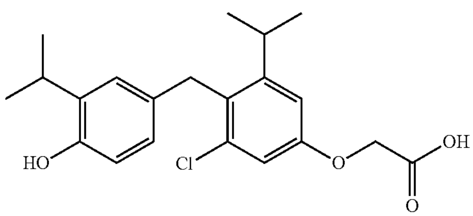 [SMILES: CC(C)c1cc(Cc2c(Cl)cc(OCC(=O)O)cc2C(C)C)ccc1O] | 2-(3-chloro-4-(4-hydroxy-3-isopropylbenzyl)-5-isopropylphenoxy)acetic acid |
| 32 | 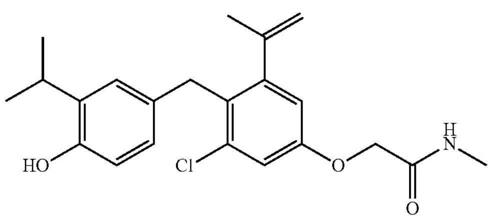 [SMILES: C=C(C)c1cc(OCC(=O)NC)cc(Cl)c1Cc1ccc(O)c(C(C)C)c1] | 2-(3-chloro-4-(4-hydroxy-3-isopropylbenzyl)-5-(prop-1-en-2-yl)phenoxy)-N-methylacetamide |
| 33 | 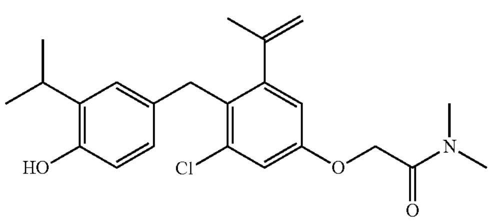 [SMILES: C=C(C)c1cc(OCC(=O)N(C)C)cc(Cl)c1Cc1ccc(O)c(C(C)C)c1] | 2-(3-chloro-4-(4-hydroxy-3-isopropylbenzyl)-5-(prop-1-en-2-yl)phenoxy)-N,N-dimethylacetamide |
| 34 | 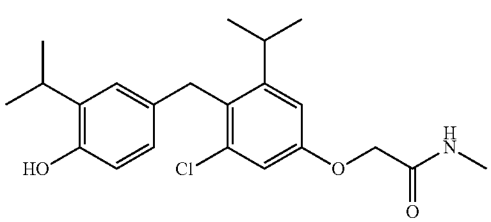 [SMILES: CNC(=O)COc1cc(Cl)c(Cc2ccc(O)c(C(C)C)c2)c(C(C)C)c1] | 2-(3-chloro-4-(4-hydroxy-3-isopropylbenzyl)-5-isopropylphenoxy)-N-methylacetamide |
| 35 | 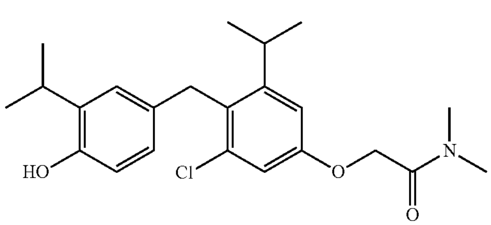 [SMILES: CC(C)c1cc(Cc2c(Cl)cc(OCC(=O)N(C)C)cc2C(C)C)ccc1O] | 2-(3-chloro-4-(4-hydroxy-3-isopropylbenzyl)-5-isopropylphenoxy)-N,N-dimethylacetamide |

TABLE 1-continued

Representative Compounds

| Cmpd. No. | Structure | Name |
|---|---|---|
| 36 | 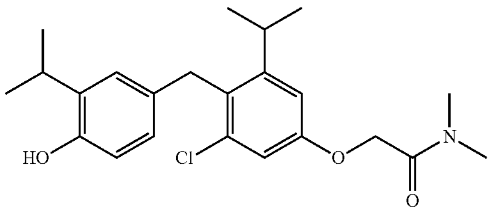 [SMILES: CC(C)c1cc(Cc2c(Cl)cc(OCC(=O)N(C)C)cc2C(C)C)ccc1O] | 2-(3-chloro-4-(4-hydroxy-3-isopropylbenzyl)-5-isopropylphenoxy)-N,N-dimethylacetamide |

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other than water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxy ethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semisolid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington; The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the Physicians' Desk Reference, incorporated herein by reference.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the neurodegenerative disease is a demyelinating disease. In another embodiment, the demyelinating disease is a chronic demyelinating disease. In yet another embodiment, the demyelinating disease is or is associated with an X-linked genetic disorder, leukodystrophy, dementia, tauopathy, or ischaemic stroke. In another embodiment, the demyelinating disease is or is associated with adult Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (HDD), infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, or Zellweger syndrome. In one embodiment, the demyelinating disease is or is associated with multiple sclerosis, MCT8 deficiency, X-linked adrenoleukodystrophy (ALD), amyotrophic lateral sclerosis (ALS), Alzheimer's disease, frontotemporal dementia, or lacunar stroke.

As used herein, the term "neurodegenerative disease" refers to any type of disease that is characterized by the progressive deterioration of the nervous system.

As used herein, the term "demyelinating disease" refers to any disease or medical condition of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "tauopathy" refers to tau-related disorders or conditions, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and mirror remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (5%) characterized by a steadily worsening disease state from onset, with acute relapses but no remissions.

In yet another embodiment, a method of treating a subject having a X-linked genetic disorder is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the X-linked genetic disorder is MCT8 deficiency or X-linked adrenoleukodystrophy (ALD).

In another embodiment, a method of treating a subject having a leukodystrophy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the leukodystrophy is adrenoleukodystrophy (ALD), adrenomyeloneuropathy (AMN), cerebral form of adrenoleukodystrophy (cALD), metachromatic leukodystrophy (MLD), Canavan's disease, or Krabbe disease (globoid leukodystrophy). As used herein, the term "adrenomyeloneuropathy" or "AMN" refers to an adult variant of X-linked adrenoleukodystrophy, characterized by ABCD1 gene mutation, that results in impaired peroxisome function with accumulation of very long chain fatty acids (VLCFA) and demyelination.

In one embodiment, a method of treating a subject having a tauopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the tauopathy is Alzheimer's disease, frontotemporal dementia, primary age-related tauopathy (PART), Pick's disease, or frontotemporal dementia and parkinsonism linked to chromosome 17 (FTDP-17).

In yet another embodiment, a method of treating a subject having an ischaemic stroke is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ischaemic stroke is lacunar stroke (also called "lacunar infarct"). In another embodiment, the present method is used to treat a subject suffering from a lacunar stroke syndrome (LACS).

In another embodiment, a method of treating a subject having adult Refsum disease, infantile Refsum disease, Alexander disease, Alzheimer's disease, halo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (HDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In one embodiment, the demyelinating disease is multiple sclerosis. In another embodiment, the demyelinating disease is X-linked adrenoleukodystrophy (ALD).

In another embodiment, a method of treating a subject having an amyotrophic lateral sclerosis (ALS) disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ALS is sporadic or familial ALS, or ALS with Superoxide dismutase-1 mutation.

In another embodiment, a method of treating a subject having a neurodevelopmental disorder is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the neurodevelopmental disorder is a demyelinating disease. In another embodiment, the demyelinating disease has adverse effects on myelination as a phenotype. In yet another embodiment, the neurodevelopmental disorder is a trisomy. In another embodiment, the neurodevelopmental disorder is Down's syndrome, or trisomy 21.

In one embodiment, a method of treating a subject having a medical condition associated with increased activity of TGF-β is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the medical condition associated with increased activity of TGF-β is a fibrotic disease. In another embodiment, the fibrotic disease is or is associated with nonalcoholic steatohepatitis (NASH), idiopathic pulmonary fibrosis (IFF), systemic scleroderma, or Alport syndrome. As used herein, the term "Alport syndrome" refers to a hereditary disorder caused by mutations in the a3a4a5(IV) collagen network genes resulting in structural defects in the glomerular basement membrane (GBM) early during development leading subsequently to the breakdown of the filtration barrier, development of renal fibrosis and kidney failure.

As used herein, the term "fibrotic disease" refers to a condition, disease or disorder that is amenable to treatment by administration of a compound having anti-fibrotic activity. Fibrotic diseases include, but are not limited to, pulmonary fibrosis, including idiopathic pulmonary fibrosis (IFF) and pulmonary fibrosis from a known etiology, liver fibrosis, and renal-fibrosis. Other exemplary fibrotic diseases include musculoskeletal fibrosis, cardiac fibrosis, post-surgical adhesions, scleroderma, glaucoma, and skin lesions such as keloids.

In another embodiment, a method of treating a subject having NASH, NAFLD, NAFLD with hyperlipidemia, alcoholic liver disease/alcoholic steatohepatitis, liver fibrosis associated with viral infection (HBV, HCV), fibrosis associated with cholestatic diseases (primary biliary cholangitis, primary sclerosing cholangitis), (familial) hypercholesterolemia, dyslipidemia, genetic lipid disorders, cirrhosis, alcohol-induced fibrosis, hemochromatosis, glycogen storage diseases, alpha-1 antitrypsin deficiency, autoimmune hepatitis, Wilson's disease, Crigler-Najjar Syndrome, lysosomal acid lipase deficiency, liver disease in cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Alport syndrome, diabetic nephropathy, FSGS, fibrosis associated with IgA nephropathy, chronic kidney diseases (CKD), post AKI, HIV associated CKD, chemotherapy induced CKD, CKD associated with nephrotoxic agents, nephrogenic systemic fibrosis, tubulointerstitial fibrosis, glomerulosclerosis, or polycystic kidney disease (PKD) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having IFF, ILD, pulmonary fibrosis, pulmonary fibrosis associated with autoimmune diseases like rheumatoid arthritis, scleroderma or Sjogren's syndrome, asthma-related pulmonary fibrosis, COPD, asbestos or silica induced PF, silicosis, respiratory bronchiolitis, Idiopathic interstitial pneumonias (IIP), Idiopathic nonspecific interstitial pneumonia, Respiratory bronchiolitis-interstitial lung disease, desquamative interstitial pneumonia, acute interstitial pneumonia, Rare IIPs: Idiopathic lymphoid interstitial pneumonia, idiopathic pieuroparenchymal fibroelastosis, unclassifiable idiopathic interstitial pneumonias, hypersensitivity pneumonitis, radiation-induced lung injury, progressive massive fibrosis—pneumoconiosis, bronchiectasis, byssinosis, chronic respiratory disease, chronic obstructive pulmonary disease (COPD), emphysema, pulmonary arterial hypertension (PAH), or Cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scleroderma/systemic sclerosis, graft versus host disease, hypertrophic scars, keloids, nephrogenic systemic fibrosis, porphyria cutanea tarda, restrictive dermopathy, Dupuytren's contracture, dermal fibrosis, nephrogenic systemic fibrosis/nephrogenic fibrosing dermopathy, mixed connective tissue disease, scleromyxedema, eosinophilic fasciitis, fibrosis caused by exposure to chemicals or physical agents. GvHD induced fibrosis, Scleredema adultorum, Lipodermatosclerosis, or Progeroid disorders (progeria, acrogeria, Werner's syndrome) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having atrial fibrosis, endomyocardial fibrosis, cardiac fibrosis, atherosclerosis, restenosis, or arthrofibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having mediastinal fibrosis, myelofibrosis, post-polycythemia vera myelofibrosis, or post essential thrombocythemia is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Crohn's disease, retroperitoneal fibrosis, intestinal fibrosis, fibrosis in inflammatory bowel disease, ulcerative colitis, GI fibrosis due to cystic fibrosis, or pancreatic fibrosis due to pancreatitis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having endometrial fibrosis, uterine fibroids, or Peyronie's disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having macular degeneration, diabetic retinopathy, retinal fibrovascular diseases, or vitreal retinopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scarring associated with trauma (surgical complications, chemotherapeutics drug-induced fibrosis, radiation induced fibrosis) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

As used herein, the term "administration" refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "chronic" refers to a medical disorder or condition that persists over time or is frequently recurring.

Compounds having the structure of Formulas (I), (II), (III) and (IV) can be synthesized using standard synthetic techniques known to those skilled in the art. For example, compounds of the present invention can be synthesized using appropriately modified synthetic procedures set forth in Scheme 1, Scheme 2, or Scheme 3.

To this end, the reactions, processes, and synthetic methods described herein are not limited to the specific conditions described in the following experimental section, but rather are intended as a guide to one with suitable skill in this field. For example, reactions may be carried out in any suitable solvent, or using other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

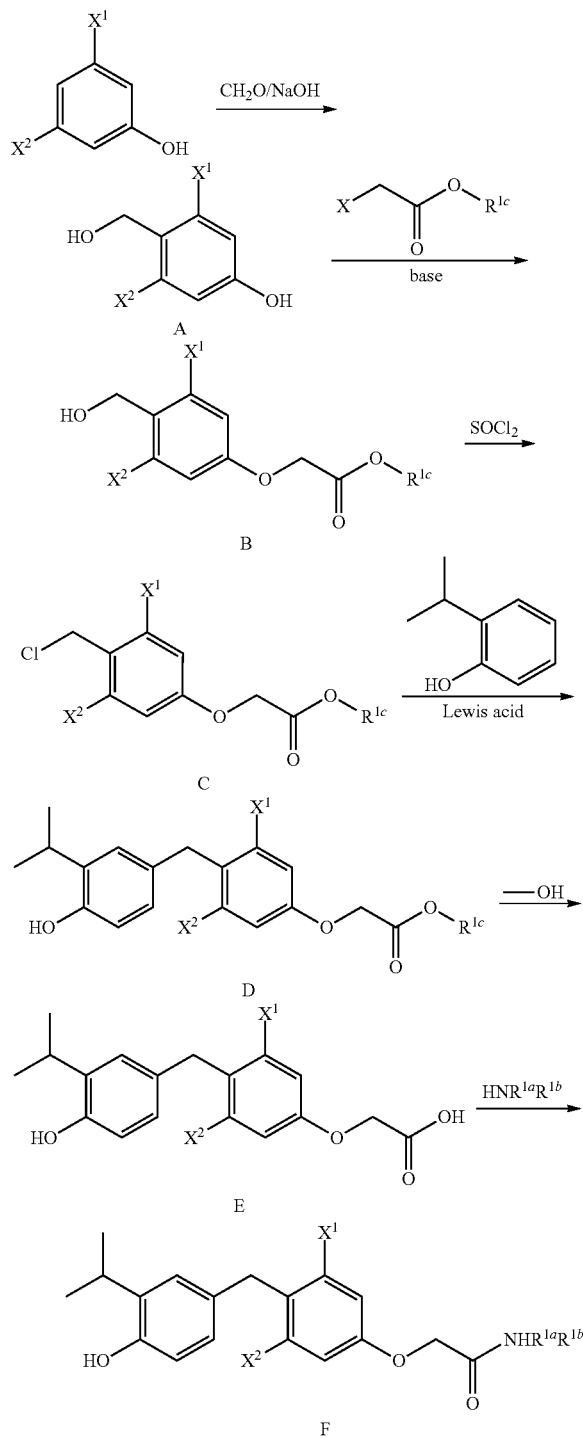

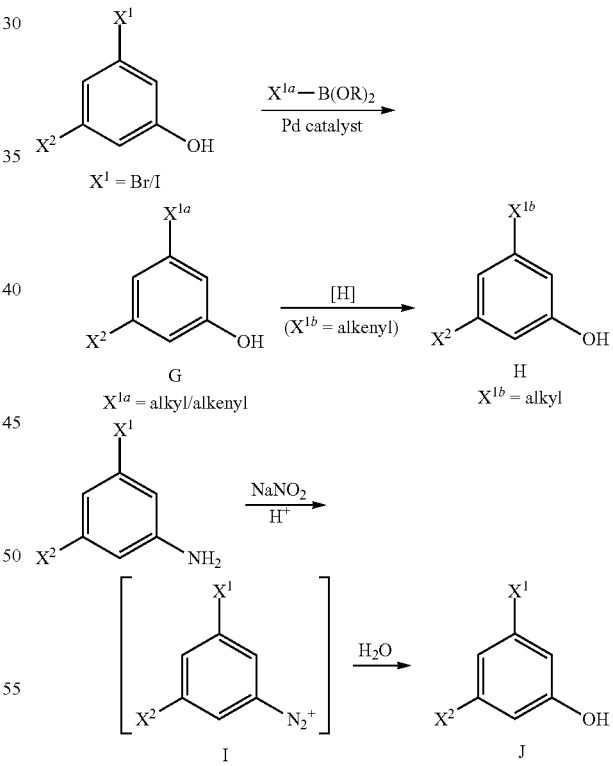

Referring to Scheme 1, a disubstituted phenol (for example, 3-methyl-5-chlorophenol or 3-methyl-5-bromophenol, or the like) is reacted with a formaldehyde equivalent (for example, aqueous formaldehyde or paraformaldehyde or dimethoxymethane or the like) to give a hydroxymethyl derivative (A), which is subsequently reacted with an activated acetate moiety (for example ethyl chloroacetate or methyl bromoacetate or the like) in the presence of base, selectively at the phenolic oxygen, to provide intermediate (B). The hydroxymethyl group is activated (for example, through reaction with thionyl chloride or oxalyl chloride or p-toluenesulfonylchloride or the like) to give a chloromethyl derivative (C) (or the corresponding tosylate, or mesylate, or bromomethyl analog, or the like), which is condensed with 2-isopropylphenol in the presence of a Lewis acid (like zinc chloride, or aluminum chloride, or the like) to give an ester (D). If desired, the ester can be hydrolyzed to give the corresponding acid (E). If desired, ester (D) can be converted to an amide (F) by heating with the corresponding amine (for example methylamine or propylamine or 2-sulfonylethylamine or the like). If desired, acid (E) can be converted to an amide (F) by condensing with the corresponding amine (for example methylamine or propylamine or 2-sulfonylethylamine or the like) in the presence of a coupling agent like DDC or EDCl or the like, or by forming an activated intermediate (for example the corresponding acid chloride) using thionyl chloride or the like.

Disubstituted phenols described in Scheme 1 may be commercially available, or may be prepared as described in Scheme 2. Referring to Scheme 2, disubstituted phenols in which one of the substituents is bromo or iodo may be reacted under Suzuki coupling conditions, for example using a boronic acid or boronate reagent or the like, in the presence of a Palladium catalyst like $Pd(OAc)_2$ or $Pd(dppf)Cl_2$ or the like, to produce alkyl or alkenyl phenols (G). In the case where $X^{1a}$ is an alkene, subsequent hydrogenation of the olefin, for example using Pd—C catalyst under a hydrogen atmosphere, can provide the corresponding alkyl-substituted (H). Alternatively, referring to Scheme 2, commercially available disubstituted anilines may be converted directly to the corresponding phenols (J) by way of the diazonium salts (I), prepared by diazotization of the aniline using $NaNO_2$ or the like, typically in acidic Solvent.

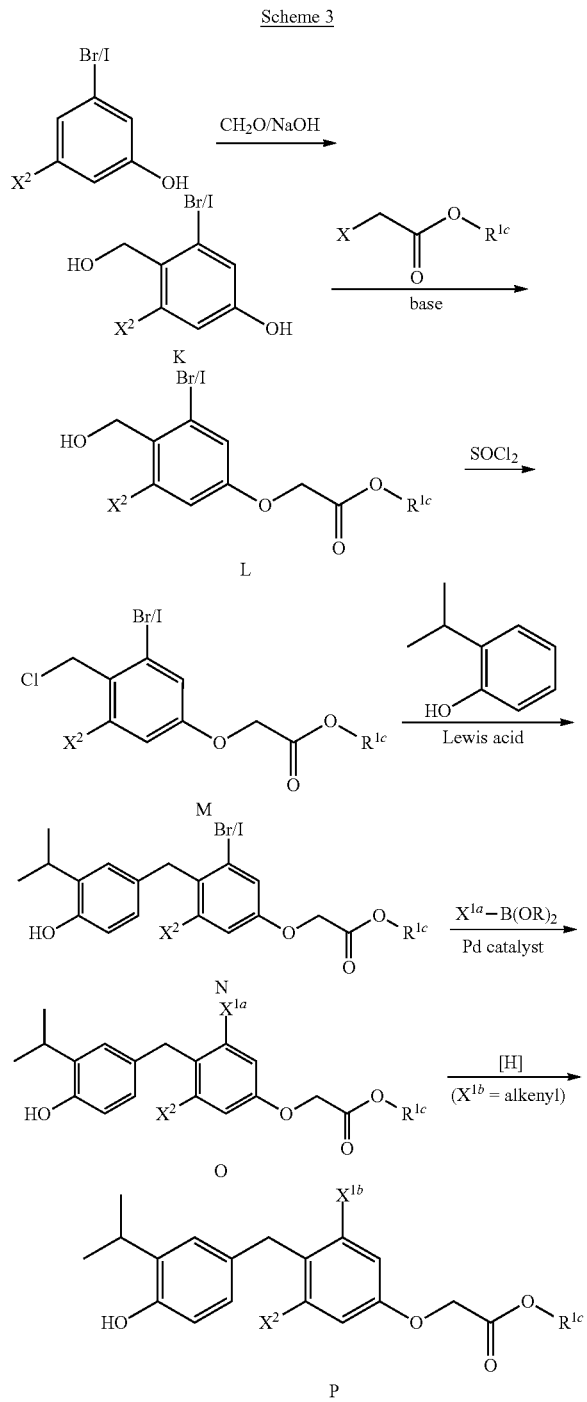

And alternative approach to the preparation of compounds of the present invention is described in Scheme 3. Disubstituted phenols having one substituent as bromine or iodine, may be converted to the corresponding advanced intermediates N by the methods described in Scheme 1. Intermediates N may be reacted under Suzuki coupling conditions, for example using a boronic acid or boronate reagent or the like, in the presence of a Palladium catalyst like $Pd(OAc)_2$ or $Pd(dppf)Cl_2$ or the like, to produce alkyl or alkenyl products (O). In the case where $X^{1a}$ is an alkene, subsequent hydrogenation of the olefin, for example using Pd—C catalyst under a hydrogen atmosphere, can provide the corresponding alkyl-substituted (P). Esters P can be further converted to the corresponding acid or amide derivatives as described in Scheme 1.

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent.

In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC using methods as described.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

All the starting materials and reagents are commercially available and were used as is. $^1H$ Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet;

dd, doublet of doublets; dt, doublet of triplets; m, multiplet; hr, broad. Preparative HPLC purification was performed by reverse phase HPLC using gradients of acetonitrile in aqueous TFA or an equivalent HPLC system such as methanol in aqueous ammonium acetate.

Chemical names were generated using the ChemDraw naming software (Version 17.0.0.206) by PerkinElmer Informatics, Inc. In some cases, generally accepted names of commercially available reagents were used in place of names generated by the naming software.

Abbreviations

The following abbreviations are used in the examples, while other abbreviations have their customary meaning in the art:

$CH_2O$: formaldehyde
$Cs_2CO_3$: cesium carbonate
d: day
DCE: dichloroethane
DCM: dichloromethane
DMF: dimethylformamide
DMSO: dimethyl sulfoxide
EDTA: ethylenediaminetetraacetic acid
ELISA: enzyme-linked immunosorbent assay
EtOAc: ethyl acetate
h: hour(s)
HCl: hydrochloric acid
HPLC: high performance liquid chromatography
$H_2SO_4$: sulfuric acid
$K_2CO_3$: potassium carbonate
l: liter
LCMS: liquid chromatography—mass spectrometry
LiOH: lithium hydroxide
M: molar
MeCN: acetonitrile
min: minute(s)
μl: microliter
ml: milliliter
$NaNO_2$: sodium nitrite
NaOH: sodium hydroxide
$Na_2SO_4$: sodium sulfate
NMP: N-methyl-2-pyrrolidone
NMR: nuclear magnetic resonance spectroscopy
PE: petroleum ether
Pd/C: palladium on carbon
RP: reverse-phase
rt: room temperature
Rt: retention time
sat.: saturated
$SOCl_2$: thionyl chloride
THF: tetrahydrofuran
$ZnCl_2$: zinc chloride

INTERMEDIATE SYNTHESIS

Synthesis of 3-chloro-4-(hydroxymethyl)-5-methyl-phenol (Intermediate A)

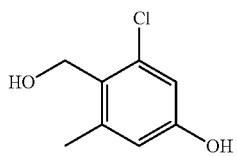

To a mixture of 3-chloro-5-methyl-phenol (3.55 g, 24.9 mmol) in water (10 mL) at rt was added NaOH (1.10 g, 27.42 mmol). The mixture was heated to 45° C., formaldehyde (0.75 g, 24.93 mmol, 37%/water) was added dropwise. The mixture was stirred at 45° C. for 2 h. The mixture was cooled down to rt, and acidified with HCl (3 N) to pH=3, extracted with EtOAc (10 mL*3). The combined EtOAc phase was washed by brine (15 mL), dried over $Na_2SO_4$, concentrated under reduced pressure. The crude product was purified by silica column (PE/EtOAc=50/1 to 5/1) to afford Intermediate A (0.76 g, 4.40 mmol, 17.7% yield) as an off-white solid. TEC: EtOAc/pet. ether=1/1(v/v), Rf=0.8 NMR (400 MHz, DMSO-$d_6$) δ 9.68 (s, 1H), 6.62 (d, J=2.4 Hz, 1H), 6.56 (d, J=2.4 Hz, 1H), 4.73 (t, J=5.2 Hz, 1H), 4.49 (d, J=5.2 Hz, 2H), 2.31 (s, 3H).

Synthesis of 3-bromo-4-(hydroxymethyl)-5-methyl-phenol (Intermediate B)

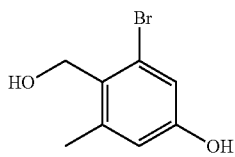

To a solution of sodium hydroxide (1.76 g, 44.11 mmol) in water (30 mL) was added 3-bromo-5-methyl-phenol (7.5 g, 40.1 mmol). The solution was heated to 45° C., formaldehyde (3.25 g, 40.1 mmol, 37%/w water) was added dropwise. The mixture was stirred at 45° C. for 2 h. The mixture was cooled down and water (10 mL) was added. The mixture was acidified with HCl (3N) to pH=3. The mixture was extracted with EtOAc (20 mL*2). The combined EtOAc phase was washed by brine (30 mL), dried over $Na_2SO_4$ and concentrated under reduced pressure. The residue was purified by silica column (pet.ether:EtOAc=30:1 to 4:1) to afford Intermediate B (1.0 g, 4.6 mmol, 11.5% yield) as a white solid. TLC: Pet. ether/EtOAc=1/1 (v/v), Rf=0.8 $^1$H NMR (400 MHz, DMSO-$d_6$) δ 9.67 (s, 1H), 6.80 (d, J=2.4 Hz, 1H), 6.60 (d, J=2.5 Hz, 1H), 4.73 (t, J=5.1 Hz, 1H), 4.51 (d, J=5.1 Hz, 2H), 2.33 (s, 3H).

Synthesis of methyl 2-[3-chloro-4-(hydroxymethyl)-5-methyl-phenoxy]acetate (Intermediate C)

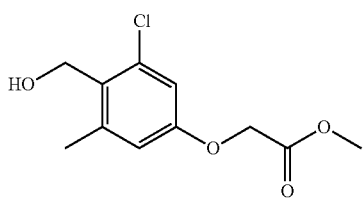

To a solution of Intermediate A (0.66 g, 3.82 mmol) in acetone (10 mL) at rt was added cesium carbonate (1.87 g, 5.74 mmol), NaI (57 mg, 382 μmol) and methyl 2-chloro-acetate (539 mg, 4.97 mmol). The mixture was stirred at rt for 4 h and water (30 mL) was added. The mixture was extracted with EtOAc (10 mL*3). The combined EtOAc phase was washed by brine (20 mL), dried over Na$_2$SO$_4$ and concentrated under reduce pressure. The crude product was purified by silica column (pet. ether/EtOAc=100/1 to 5/1) to afford Intermediate C (280 mg, 1.14 mmol, 29.9% yield) as a white solid. TLC: EtOAc/pet.ether=1/2(v/v), Rf=0.67 $^1$H NMR (400 MHz, DMSO-d$_6$) δ 6.84 (d, J=2.6 Hz, 1H), 6.78 (d, J=2.6 Hz, 1H), 4.85-4.81 (m, 3H), 4.53 (d, J=4.9 Hz, 2H), 3.69 (s, 2H), 2.37 (s, 3H).

Synthesis of methyl 2-[3-bromo-4-(hydroxymethyl)-5-methyl-phenoxy]acetate (Intermediate D)

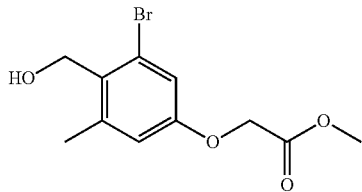

To a solution of Intermediate B (900 mg, 4.15 mmol) in acetone (15 mL) was added NaI (63 mg, 41.5 μmol) and Cs$_2$CO$_3$ (2.03 g, 6.2 mmol). Methyl 2-chloroacetate (585 mg, 5.4 mmol) was added dropwise. The mixture was refluxed for 2 h. The mixture was cooled down and filtered. The filtrate was diluted with EtOAc (30 mL) and water (50 mL). The organic phase was washed with brine (30 mL), dried over Na$_2$SO$_4$ and concentrated in vacuum. The residue was purified by silica column (pet. ether:EtOAc=30:1-3:1) to afford Intermediate D (360 mg, 1.25 mmol, 30.0% yield) as a white solid. TLC: Pet.ether/EtOAc=2/1(v/v), Rf=0.7 $^1$H NMR (400 MHz, DMSO-d$_6$) δ 7.00 (d, J=2.6 Hz, 1H), 6.82 (d, J=2.7 Hz, 1H), 4.84 (t, J=5.2 Hz, 1H), 4.82 (s, 2H), 4.55 (d, J=5.2 Hz, 2H), 3.69 (s, 3H), 2.39 (s, 3H).

Synthesis of methyl 2-[3-chloro-4-(chloromethyl)-5-methyl-phenoxy]acetate (Intermediate E)

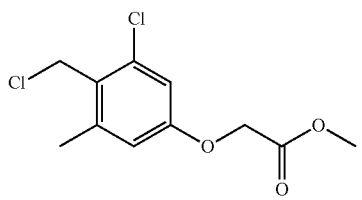

To a solution of Intermediate C (360 mg, 1.47 mmol) in DCM (6 mL) at rt was added thionyl chloride (263 mg, 2.21 mmol). The mixture was stirred at rt for 1 h, then concentrated under reduced pressure to afford Intermediate E (300 mg, 1.14 mmol, 77.5% yield) as a yellow solid. TLC: EtOAc/pet. ether=1/2(v/v), Rf=0.8 $^1$H NMR (400 MHz, DMSO-d$_6$) δ 6.96 (d, J=2.4 Hz, 1H), 6.87 (d, J=2.4 Hz, 1H), 4.86 (s, 2H), 4.82 (s, 2H), 3.71 (s, 3H), 2.41 (s, 3H).

Synthesis of methyl 2-[3-bromo-4-(chloromethyl)-5-methyl-phenoxy]acetate (Intermediate F)

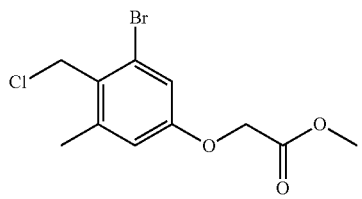

To a solution of Intermediate D (100 mg, 346 μmol) in dichloromethane (4 mL) was added thionyl chloride (82.3 mg, 692 μmol). The mixture was stirred at rt for 1 h. The mixture was concentrated in vacuum to afford Intermediate F (100 mg, 325 μmol, 94.0% yield) as a white solid. TLC: Pet. ether/EtOAc=2/1 (v/v), Rf=0.8 $^1$H NMR (400 MHz, DMSO-d$_6$) δ 7.11 (d, J=2.6 Hz, 1H), 6.91 (d, J=2.6 Hz, 1H), 4.86 (s, 2H), 4.84 (s, 2H), 3.70 (s, 3H), 2.42 (s, 3H).

Synthesis of 3-chloro-5-vinylphenol (Intermediate G)

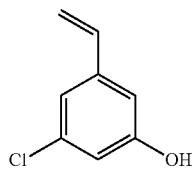

To a solution of 3-bromo-5-chlorophenol (10 g, 48.2 mmol), 2,3-dimethylbutane-2,3-diol vinylboronic acid (11.1 g, 72.31 mmol) and diacetoxypalladium (1.08 g, 4.82 mmol) in toluene (100 mL) at rt was added tricyclohexylphosphine (2.70 g, 9.64 mmol). The mixture was refluxed overnight. The mixture was poured into water (20 mL) and extracted with EtOAc (20 mL*2). The combined organic phase was washed with brine (20 mL), dried over Na$_2$SO$_4$, and concentrated in vacuo. The residue was purified by silica gel chromatography (pet.ether:EtOAc=100:1 to 40:1) to afford Intermediate G (4.0 g, 37% yield) as a yellow oil. TLC: Pet. ether/EtOAc=5/1 (v/v), Rf=0.6 $^1$H NMR (400 MHz, DMSO-d$_6$) δ 9.90 (s, 1H), 6.97 (t, J=1.7 Hz, 1H), 6.81-6.79 (m, 1H), 6.71 (t, J=2.1 Hz, 1H), 6.62 (dd, J=17.6, 10.9 Hz, 1H), 5.81 (dd, J=17.6, 0.8 Hz, 1H), 5.28 (dd, J=10.9, 0.8 Hz, 1H).

Synthesis of 3-chloro-5-ethylphenol (Intermediate H)

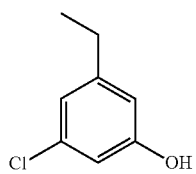

To a solution of Intermediate G (4.0 g, 25.9 mmol) in THF (40 mL) was added Pd/C (400 mg). The mixture was stirred at rt for 8 h under H₂ atmosphere. The mixture was filtered through Celite to remove catalyst and concentrated in vacuo to afford Intermediate H (4.0 g, 98.7% yield) as a yellow oil. TLC: Pet. ether/EtOAc=5/1 (v/v), Rf=0.6 NMR (400 MHz, DMSO-d₆) δ 9.81 (s, 1H), 6.68 (t, J=1.7 Hz, 1H), 6.61 (t, j=2.1 Hz, 1H), 6.57 (dd, j=2.3, 1.4 Hz, 1H), 2.50 (q, j=7.6 Hz, 2H), 1.13 (t, 7=7.6 Hz, 3H).

Synthesis of
3-chloro-5-ethyl-4-(hydroxymethyl)phenol
(Intermediate I)

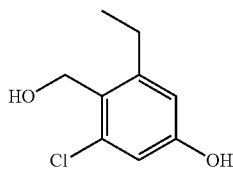

I

To a solution of Intermediate H (4.0 g, 25.5 mmol) and sodium hydroxide (1.12 g, 28.1 mmol) in water (30 mL), warmed to 55° C., was added formaldehyde (37%/w). The resulting mixture was stirred at 45° C. for 16 h. The reaction was acidified to pH=6-7 with 2N HCl, and extracted with EtOAc (20 mL*2). The combined EtOAc phase was washed with brine (30 mL), dried over Na₂SO₄, concentrated in vacuo and purified by reversed-phase column to afford Intermediate I (200 mg, 4% yield). TEC: Pet. ether/EtOAc=3/1(v/v), Rf=0.5 ¹H NMR (400 MHz, DMSO-d₆) δ 9.70 (s, 1H), 6.64 (d, J=2.4 Hz, 1H), 6.58 (d, J=2.5 Hz, 1H), 4.76 (t, J=5.0 Hz, 1H), 4.50 (d, J=5.0 Hz, 2H), 2.67 (q, J=7.5 Hz, 2H), 1.14 (t, J=7.5 Hz, 3H).

Synthesis of ethyl 2-(3-chloro-5-ethyl-4-(hydroxymethyl)phenoxy)acetate (Intermediate J)

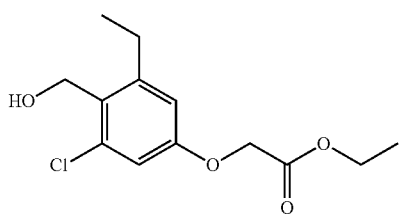

J

To a solution of Intermediate I (200 mg, 1.07 mmol) in DMF (20 mL) at rt was added Potassium carbonate (177 mg, 1.28 mmol) and ethyl 2-bromoacetate (232 mg, 1.39 mmol); the resulting mixture was stirred at rt for 1 h. Water (100 mL) was added; the mixture was extracted with EtOAc (30 mL*2). The combined organic phase was washed with brine (50 mL), dried over Na₂SO₄, and concentrated in vacuo to afford Intermediate J (270 mg, 92% yield) as a white solid. TEC: Pet. ether/EtOAc=2/1 (v/v), Rf=0.7 ¹H NMR (400 MHz, DMSO-d₆) δ 6.84 (d, J=2.6 Hz, 1H), 6.77 (d, J=2.7 Hz, 1H), 4.88 (t, J=5.1 Hz, 1H), 4.80 (s, 2H), 4.54 (d, J=5.1 Hz, 2H), 4.17 (q, 7=7.1 Hz, 2H), 2.72 (q, J=7.5 Hz, 2H), 1.21 (t, 7=7.1 Hz, 3H), 1.16 (t, J=7.5 Hz, 3H).

Synthesis of ethyl
2-(3-chloro-4-(chloromethyl)-5-ethylphenoxyacetate
(Intermediate

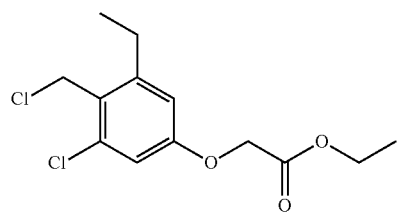

K

To a solution of Intermediate J (270 mg, 0.99 mmol) in DCM (10 mL) at rt was added thionyl chloride (235 mg, 1.98 mmol); the resulting mixture was stirred at rt for 1 hr. The reaction mixture was concentrated in vacuo to afford Intermediate K (280 mg, 97% yield) as a yellow solid. TLC: Pet. ether/EtOAc=5/1 (v/v), Rf=0.7 ¹H NMR (400 MHz, DMSO-d₆) δ 6.97 (d, J=2.6 Hz, 1H), 6.84 (d, J=2.7 Hz, 1H), 4.85 (s, 2H), 4.83 (s, 2H), 4.17 (q, J=7.1 Hz, 2H), 2.73 (q, J=7.6 Hz, 2H), 1.20-1.20 (m, 6H).

Synthesis of 3-methyl-5-(trifluoromethyl)phenol
(Intermediate L)

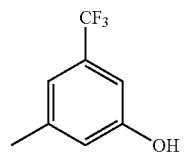

L

A mixture of 3-methyl-5-(trifluoromethyl)aniline (3.5 g, 20 mmol) in water (200 mL) and con. H₂SO₄ (40 mL) was cooled down to 0° C., NaNO₂ (1.45 g, 21 mmol) in water (1 mL) was added dropwise. The reaction was stirred at 0° C. for 30 min, con.H₂SO₄ (40 mL) was added and the mixture was heated to 90° C. overnight. The mixture was cooled to rt and extracted with EtOAc (20 mL*2); the combined organic phase was washed with brine, dried over Na₂SO₄, and concentrated in vacuo to afford Intermediate L (3.0 g, 85% yield) as a yellow oil. TLC: EtOAc/pet. ether=1/10(v/v), Rf=0.47 ¹H NMR (400 MHz, DMSO-d₆) δ 9.97 (s, 1H), 6.93 (s, 1H), 6.85 (s, 1H), 6.83 (d, J=2.1 Hz, 1H), 2.30 (s, 3H).

Synthesis of 4-(hydroxymethyl)-3-methyl-5-(trifluoromethyl)phenol (Intermediate M)

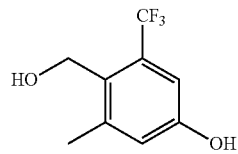

M

To a solution of Intermediate L (3.5 g, 19.8 mmol) and NaOH (0.95 g, 23.8 mmol) in water (70 mL) at 50° C. was added formaldehyde (1.62 g, 19.8 mmol). The reaction was stirred at 50° C. overnight. The reaction mixture was acidified to pH=6-7 with 1N HCl and extracted with EtOAc (50 mL*3); the combined organic phase was washed with brine (20 mL), dried over Na$_2$SO$_4$, concentrated under reduced pressure. The crude product was purified by silica gel chromatography (pet. ether/EtOAc=50/1 to 10/1 to 3/1) to afford Intermediate M (200 mg, 5% yield) as an off-white solid. TLC: EtOAc/pet. ether=1/5(v/v), Rf=0.37 $^1$H NMR (400 MHz, DMSO-d$_6$) δ 9.95 (s, 1H), 6.94 (d, J=1.5 Hz, 1H), 6.92 (s, 1H), 4.81 (s, 1H), 4.54 (s, 2H), 2.27 (s, 3H).

Synthesis of ethyl 2-(4-(hydroxymethyl)-3-methyl-5-(trifluoromethyl)phenoxy)acetate (Intermediate N)

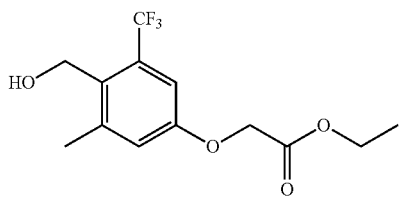

N

To a solution of Intermediate M (150 mg, 0.73 mmol) in DMF (5 mL) was added K$_2$CO$_3$ (151 mg, 1.09 mmol) and Ethyl bromoacetate (134 mg, 0.8 mmol). The reaction was stirred at rt overnight. Water (40 mL) was added, and the mixture was extracted with EtOAc (20 mL*2). The combined organic phase was washed by brine (40 mL), dried over Na$_2$SO$_4$, and concentrated in vacuo to afford Intermediate N (160 mg, 75% yield) as a yellow oil. TLC: EtOAc/pet. ether=1/5(v/v), Rf=0.54 $^1$H NMR (400 MHz, DMSO-d$_6$) δ 7.45 (d, J=2.7 Hz, 1H), 7.37 (d, J=2.7 Hz, 1H), 5.02 (s, 2H), 4.19 (q, J=7.1 Hz, 3H), 2.31 (s, 3H), 1.22-1.19 (m, 3H).

Synthesis of ethyl 2-(4-(chloromethyl)-3-methyl-5-(trifluoromethyl)phenoxy)acetate (Intermediate O)

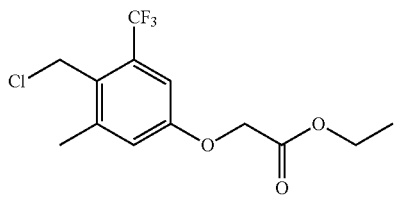

O

To a solution of Intermediate N (160 mg, 0.54 mmol) in DCM (5 mL) at 0° C. was added SOCl$_2$ (77 mg, 0.65 mmol). The mixture was stirred at 0° C. for 2 h. The mixture was concentrated to dryness to afford product Intermediate O (160 mg, 94% yield) as a yellow solid, used directly in the next step. TLC: EtOAc/pet. ether=1/5(v/v), Rf=0.74.

Synthesis of ethyl 2-(3-bromo-4-(hydroxymethyl)-5-methylphenoxy)acetate (Intermediate P)

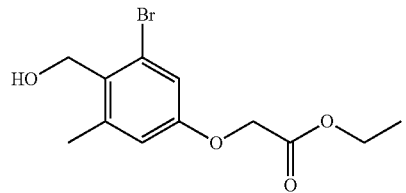

P

To a solution of Intermediate B (1.0 g, 4.6 mmol) and sodium bicarbonate (657 mg, 7.8 mmol) in DMF (10 mL) at rt was added ethyl 2-bromoacetate (1.0 g, 6.0 mmol). The mixture was stirred at rt overnight. Water (20 mL) was added, and the mixture was extracted with EtOAc (20 mL*2). The combined organic phase was washed with brine (30 mL), dried over Na$_2$SO$_4$, and concentrated under reduced pressure. The residue was purified by silica gel chromatography (pet.ether:EtOAc=100:1 to 5:1) to afford Intermediate P (600 mg, 42% yield) as a white solid. TLC: Pet. ether/EtOAc=2/1(v/v), Rf=0.7 $^1$H NMR (400 MHz, DMSO-d$_6$) δ 6.99 (d, J=2.8 Hz, 1H), 6.83-6.80 (m, 1H), 4.85 (t, J=5.2 Hz, 1H), 4.79 (s, 2H), 4.55 (d, J=5.2 Hz, 2H), 4.17 (q, J=12 Hz, 2H), 2.38 (s, 3H), 1.21 (t, J=12 Hz, 3H).

Synthesis of ethyl 2-(3-bromo-4-(chloromethyl)-5-methylphenoxy)acetate (Intermediate

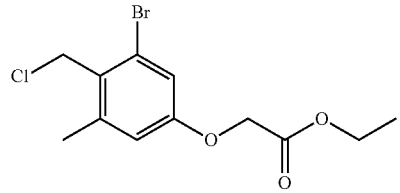

Q

To a solution of Intermediate P (600 mg, 1.98 mmol) in dichloromethane (10 mL) at rt was added thionyl chloride (471 mg, 3.96 mmol). The mixture was stirred at rt 1 h and concentrated in vacuo to afford Intermediate Q (600 mg, 94% yield) as a white solid. TLC: Pet. ether/EtOAc=2/1(v/v), Rf=0.8 $^1$H NMR (400 MHz, DMSO-d$_6$) δ 7.10 (d, J=2.8 Hz, 1H), 6.92-6.89 (m, 1H), 4.84 (s, 4H), 4.17 (q, J=12 Hz, 2H), 2.42 (s, 3H), 1.21 (t, J=12 Hz, 3H).

Synthesis of 3-chloro-4-(hydroxymethyl)-5-(trifluoromethyl)phenol (Intermediate R)

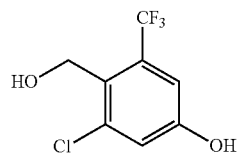

R

To a solution of NaOH (2.70 g, 67.2 mmol) in H₂O (40 mL) at rt was added 3-chloro-5-trifluoromethyl-phenol (4.00 g, 20.4 mmol). The mixture was heated to 45° C., and formaldehyde (8.65 g, 100 mmol, 37% purity) was added dropwise. The mixture was stirred at 45° C. for 3d, diluted with water (20 mL), acidified with 2 N HCl to pH=5-6 with 1N HCl, extracted with EtOAc (10 mL*3). The combined organic phase was washed with brine (10 mL), dried over Na₂SO₄, and concentrated under reduced pressure. The crude product was purified on a silica column (pet. ether/EtOAc=20/1 to 10/1) to afford Intermediate R (0.42 g, 1.85 mmol, 9% yield) as an off-white solid. TLC: EtOAc/pet.ether=1/5(v/v), Rf=0.41 ¹H NMR (400 MHz, DMSO-d₆) δ 10.54 (s, 1H), 7.13 (d, J=2.5 Hz, 1H), 7.05 (d, J=2.5 Hz, 1H), 5.01 (t, J=5.0 Hz, 1H), 4.58-4.54 (d, J=5.2 Hz, 2H).

Synthesis of ethyl 2-(3-chloro-4-(hydroxymethyl)-5-(trifluoromethyl)phenoxy)acetate (Intermediate S)

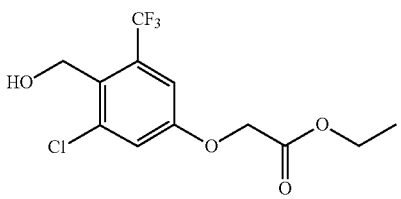

To a solution of Intermediate R (0.4 g, 1.8 mmol) in DMF (4 mL) at rt was added potassium carbonate (293 mg, 2.1 mmol) and ethyl bromoacetate (295 mg, 1.8 mmol). The mixture was stirred at 50° C. for 6 h. The reaction mixture was cooled down to rt, quenched with water (20 mL), extracted with EtOAc (5 mL*3). The combined organic phase was washed with water (5 mL*5) and brine (5 mL), dried over Na₂SO₄, and concentrated under reduced pressure to afford Intermediate S (0.52 g, 1.66 mmol, 94% yield) as an off-white solid. TLC: EtOAc/pet. ether=1/5(v/v), Rf=0.45 ¹H NMR (400 MHz, DMSO-d₆) δ 7.43 (d, j=2.6 Hz, 1H), 7.23 (d, j=2.6 Hz, 1H), 5.13 (t, j=5.0 Hz, 1H), 4.97 (s, 2H), 4.60 (d, j=4.7 Hz, 2H), 4.18 (q, j=7.1 Hz, 2H), 1.21 (t, 7=7.1 Hz, 3H).

Synthesis of ethyl 2-(3-chloro-4-(chloromethyl)-5-(trifluoromethyl)phenoxy)acetate (Intermediate T)

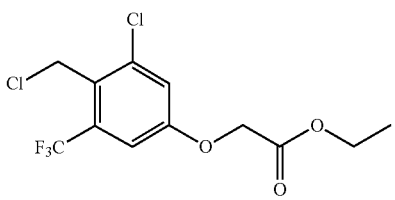

To solution of Intermediate S (0.31 g, 0.99 mmol) in DCM (3 mL) at ice-bath temperature was added SOCl₂ (177 mg, 1.5 mmol). The mixture was stirred at rt for 2 h, diluted with DCM (10 mL), and concentrated under reduced pressure to afford Intermediate T (310 mg, 0.94 mmol, 94% yield) as a yellow oil. TLC: EtOAc/pet. ether=1/5(v/v), R_f=0.85 NMR (400 MHz, DMSO-d₆) δ 7.55 (d, J=2.7 Hz, 1H), 7.33 (d, J=2.7 Hz, 1H), 5.01 (s, 2H), 4.83 (s, 2H), 4.18 (q, J=7.1 Hz, 2H), 1.21 (t, J=7.1 Hz, 3H).

Synthesis of 3-bromo-5-chloro-4-(hydroxymethyl)phenol (Intermediate U)

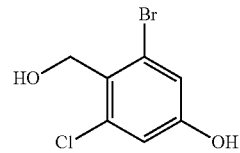

To a solution of 3-bromo-5-chlorophenol (2.0 g, 9.6 mmol) and NaOH (420 mg, 10.6 mmol) in water (30 mL) at 45° C. was added formaldehyde (780 mg, 9.6 mmol). The reaction was stirred at 45° C. overnight. The reaction mixture was acidified to pH 6-7 with 1N HCl, then extracted with EtOAc (20 mL*3). The combined organic phase was washed with brine (20*2 mL), dried over Na₂SO₄, and concentrated under reduced pressure. The crude product was purified by reverse-phase column chromatography (35% MeCN in water) to afford Intermediate U (1.0 g, 43% yield) as an off-white solid. TLC: EtOAc/pet. ether=1/5(v/v), Rf=0.41 ¹H NMR (400 MHz, DMSO-d₆) δ 10.313 (s, 1H), 6.99 (d, J=2.4 Hz, 1H), 6.86 (d, J=2.4 Hz, 1H), 4.98 (t, J=5.2 Hz, 1H), 4.59 (d, J=5.2 Hz, 2H).

Synthesis of ethyl 2-(3-bromo-5-chloro-4-(hydroxymethyl)phenoxy)acetate (Intermediate V)

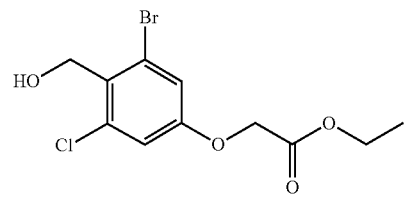

A mixture of Intermediate U (1.0 g, 4.2 mmol), ethyl bromoacetate (840 mg, 5.05 mmol) and K₂CO₃ (870 mg, 6.3 mmol) in DMF (15 mL) was stirred at rt for 1 h. Water (30 mL) was added, and the resultant mixture was extracted with EtOAc (25 mL). The combined organic phase was washed with water (25*3 mL), and brine (50 mL), dried over Na₂SO₄, and concentrated to dryness to afford Intermediate V (1.1 g, 80% yield) as a white solid. TLC: EtOAc/pet. ether=1/5(v/v), Rf=0.54 ¹H NMR (400 MHz, DMSO-d₆) δ 7.23 (d, J=2.4 Hz, 1H), 7.13 (d, J=2.4 Hz, 1H), 5.08 (t, J=5.2 Hz, 1H), 4.89 (s, 2H), 4.63 (d, j=5.2 Hz, 2H), 4.17 (q, j=12 Hz, 2H), 1.21 (t, j=12 Hz, 3H).

Synthesis of ethyl 2-(3-bromo-5-chloro-4-(chloromethyl)phenoxy)acetate (Intermediate

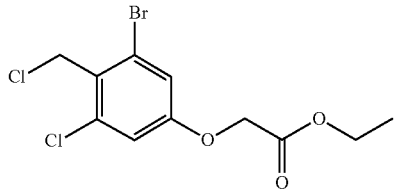

W

To a solution of Intermediate V (1.1 g, 3.40 mmol) in DCM (15 mL) at 0° C. was added SOCl$_2$ (485 mg, 4.08 mmol). The mixture was stirred at 0° C. for 2 h. The mixture was concentrated to dryness to afford Intermediate W (1.1 g, 94% yield) as a yellow solid. TLC: EtOAc/pet. ether=1/5 (v/v), Rf=0.74 $^1$H NMR (400 MHz, DMSO-d$_6$) δ 7.34 (d, j=2.4 Hz, 1H), 7.24 (d, j=2.8 Hz, 1H), 4.93 (s, 2H), 4.88 (s, 2H), 4.17 (q, j=12 Hz, 2H), 1.21 (t, j=12 Hz, 3H).

Example 1

Synthesis of methyl 2-(3-chloro-4-(4-hydroxy-3-isopropylbenzyl)-5-methylphenoxy)acetate (Compound 1)

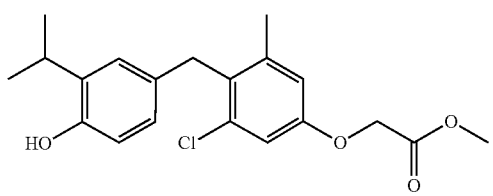

1

To a solution of Intermediate E (300 mg, 1.14 mmol) in 1,2-dichloroethane (6 mL) at rt was added zinc chloride (2.85 mL, 2.85 mmol, 1M in Hexane) and 2-isopropylphenol (466 mg, 3.42 mmol). The mixture was stirred at 85° C. overnight. The solution was diluted with water (20 mL), and extracted with DCM (10 mL*3). The combined DCM phase was washed by brine (15 ml), dried over Na$_2$SO$_4$ and concentrated under reduce pressure. The crude product was purified by Prep-TLC (PE/EtOAc=1/3) to afford Compound 1 (90 mg, 248.04 μmol, 21.7% yield) as a white solid. TLC: EtOAc/pet. ether=1/3(v/v), Rf=0.45 HNMR: $^1$H NMR (400 MHz, DMSO-d$_6$) δ 9.03 (s, 1H), 6.92 (d, J=2.7 Hz, 1H), 6.90 (d, J=2.2 Hz, 1H), 6.80 (d, J=2.7 Hz, 1H), 6.63 (d, J=8.2 Hz, 1H), 6.56 (dd, J=8.2, 2.2 Hz, 1H), 4.81 (s, 2H), 3.93 (s, 2H), 3.70 (s, 3H), 3.12 (hept, J=6.9 Hz, 1H), 2.19 (s, 3H), 1.10 (d, J=6.9 Hz, 6H).

Example 2

Synthesis of 2-(3-chloro-4-(4-hydroxy-3-isopropylbenzyl)-5-methyl phenoxyacetic acid (Compound 2)

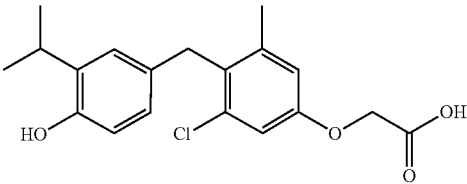

2

To a solution of Compound 1 (40 mg, 110 μmol) in THF/H$_2$O (4 mL/6 mL) at rt was added NaOH (9 mg, 220 μmol). The mixture was stirred for 2 h, extracted with ether (10 mL). The aqueous phase was acidified with HCl (2 N) to pH=3, extracted with EtOAc (10 mL*3). The combined EtOAc phase was washed by brine (10 mL), dried over Na$_2$SO$_4$ and concentrated under reduce pressure. The crude product was purified by Prep-HPLC (MeCN/water range from 30/70 to 85/15, 35 min) to afford Compound 2 (13 mg, 37.27 μmol, 33.8% yield) as a white solid. TEC: Pet. ether/EtOAc=1/1(v/v), Rf=0.1 HNMR: NMR (400 MHz, DMSO-d$_6$) δ 9.03 (s, 1H), 6.91 (d, J=2.2 Hz, 1H), 6.87 (d, J=2.7 Hz, 1H), 6.77 (d, J=2.7 Hz, 1H), 6.63 (d, J=8.2 Hz, 1H), 6.56 (dd, J=8.2, 2.2 Hz, 1H), 4.66 (s, 2H), 3.93 (s, 2H), 3.16-3.09 (m, 1H), 2.19 (s, 3H), 1.10 (d, 7=6.9 Hz, 6H).

Example 3

Synthesis of 2-(3-chloro-4-(4-hydroxy-3-isopropylbenzyl)-5-methylphenoxy)-N-methylacetamide (Compound 3)

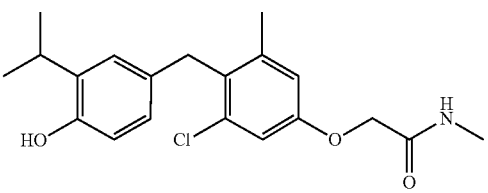

3

To a solution of Compound 1 (40 mg, 110 μmol) in THF (4 mL) at rt was added methylamine (4 mL, 40%/w water). The reaction was stirred at 65° C. overnight. The mixture was diluted with water (10 mL), extracted with EtOAc (10 mL*3). The combined EtOAc phase was washed by brine (10 mL), dried over Na$_2$SO$_4$, concentrated under reduce pressure and purified by prep-HPLC (MeCN/water range from 30/70 to 85/15) to afford Compound 3 (12 mg, 33.16 μmol, 30.1% yield) as a white solid. TEC: Pet. ether/EtOAc=5/1(v/v), Rf=0.2 HNMR: $^1$H NMR (400 MHz, DMSO-d$_6$) δ 9.03 (s, 1H), 8.02 (brs, 1H), 6.94 (d, J=2.6 Hz, 1H), 6.90 (d, J=2.2 Hz, 1H), 6.83 (d, J=2.6 Hz, 1H), 6.62 (d, J=8.2 Hz, 1H), 6.56 (dd, J=8.2, 2.2 Hz, 1H), 4.46 (s, 2H), 3.94 (s, 2H), 3.17-3.08 (m, 1H), 2.65 (d, J=4.6 Hz, 3H), 2.20 (s, 3H), 1.10 (d, J=6.9 Hz, 6H).

Example 4

Synthesis of methyl 2-(3-bromo-4-(4-hydroxy-3-isopropylbenzyl)-5-methylphenoxy)acetate (Compound 4)

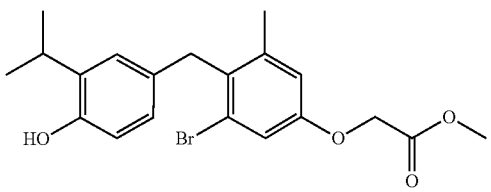

To a solution of Intermediate F (100 mg, 346 μmol) in 1,2-dichloroethane (3 mL) at rt was added ZnCl$_2$ (0.86 mL, 865 μmol, 1.0M in hexane), 2-isopropylphenol (141 mg, 1.04 mmol). The mixture was heated to 85° C. overnight. The reaction was cooled down to rt. DCM (10 mL) was added. The mixture was washed with water (10 mL), brine (10 mL), dried over Na$_2$SO$_4$ and concentrated under reduce pressure. The crude product was purified by prep-TLC (pet.ether/EtoAe=3/1) to afford to afford Compound 4 (60 mg, 147 μmol, 42.6% yield) as a white solid. TLC: Pet. ether/EtOAc=3/1(v/v), Rf=0.5 HNMR: $^1$H NMR (400 MHz, DMSO-d$_6$) δ 9.03 (s, 1H), 7.07 (d, J=2.7 Hz, 1H), 6.90 (d, J=2.2 Hz, 1H), 6.84 (d, J=2.7 Hz, 1H), 6.63 (d, J=8.2 Hz, 1H), 6.55 (dd, J=8.2, 2.2 Hz, 1H), 4.81 (s, 2H), 3.97 (s, 2H), 3.70 (s, 3H), 3.15-3.08 (m, 1H), 2.19 (s, 3H), 1.10 (d, 7=6.9 Hz, 6H).

Example 5

Synthesis of 2-(3-bromo-4-(4-hydroxy-3-isopropylbenzyl)-5-methyl phenoxyacetic acid (Compound 5)

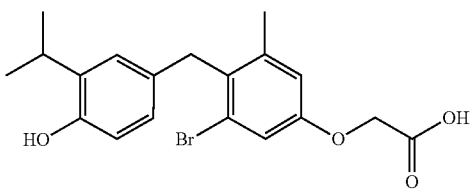

To a solution of Compound 4 (100 mg, 246 μmol) in THF (4 mL) and water (1 mL) was added LiOH·H$_2$O (30 mg, 0.72 mmol). The mixture was stirred at rt for 1 h. The mixture was concentrated and water (10 mL) was added. The mixture was extracted with ether (10 mL*2). Aqueous phase was adjusted to pH=3 with HCl (1N) and was extracted with EtOAc (10 mL*2). The combined organic phase was washed by brine (20 mL), dried over Na$_2$SO$_4$ and concentrated under reduced pressure to afford Compound 5 (70 mg, 178 μmol, 72.5% yield) as a white solid. TEC; Pet. ether/EtOAc=1/1 (v/v), Rf=0.1 HNMR: NMR (400 MHz, DMSO-d$_6$) δ 9.05 (s, 1H), 7.03 (d, J=2.7 Hz, 1H), 6.91 (d, J=2.2 Hz, 1H), 6.81 (d, J=2.7 Hz, 1H), 6.63 (d, J=8.2 Hz, 1H), 6.55 (dd, J=8.2, 2.2 Hz, 1H), 4.66 (s, 2H), 3.97 (s, 2H), 3.12 (hept, J=6.9 Hz, 1H), 2.19 (s, 3H), 1.10 (d, J=6.9 Hz, 6H).

Example 6

Synthesis of 2-(3-bromo-4-(4-hydroxy-3-isopropylbenzyl)-5-methylphenoxy)-N-methylacetamide (Compound 6)

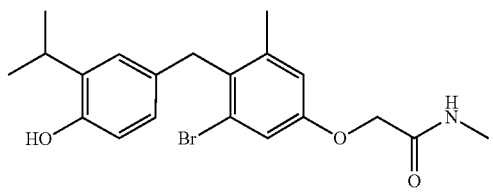

To a solution of Compound 4 (130 mg, 0.32 mmol) in THF (5 mL), was added methylamine (8 mL, 40%/w water). The reaction was stirred at 65° C. overnight. The mixture was cooled down and water (20 mL) was added. The mixture was extracted with EtOAc (10 mL*2). The combined organic phase was washed by brine (20 mL), dried over Na$_2$SO$_4$ and concentrated under reduced pressure. The crude product was purified by prep-HPLC (MeCN/water from 30/80 to 90/20) to afford Compound 6 (60 mg, 148 μmol, 60.2% yield) as a white solid. TEC: Pet. ether/EtOAc=5/1 (v/v), Rf=0.2 HNMR: NMR (400 MHz, DMSO-d$_6$) δ 9.03 (s, 1H), 8.02 (brs, 1H), 7.11 (d, J=2.7 Hz, 1H), 6.90 (d, J=2.2 Hz, 1H), 6.86 (d, J=2.7 Hz, 1H), 6.62 (d, J=8.2 Hz, 1H), 6.55 (dd, J=8.2, 2.2 Hz, 1H), 4.46 (s, 2H), 3.98 (s, 2H), 3.16-3.08 (m, 1H), 2.65 (d, J=4.6 Hz, 3H), 2.20 (s, 3H), 1.10 (d, 7=6.9 Hz, 6H).

Example 7

Synthesis of ethyl 2-(3-chloro-5-ethyl-4-(4-hydroxy-3-isopropylbenzyl)phenoxy)acetate (Compound 7)

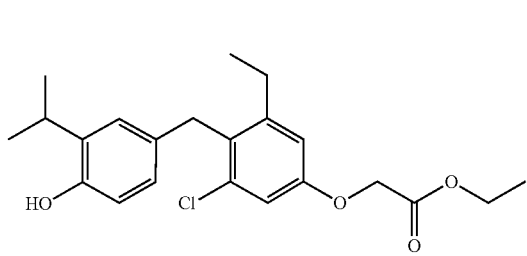

To a solution of Intermediate K (280 mg, 0.96 mmol) in 1,2-dichloroethane (10 mL) at rt was added 2-isopropylphenol (393 mg, 2.88 mmol) and Zinc chloride (1.0M in THF, 3 mL, 2.88 mmol). The reaction was heated to 90° C. and stirred overnight. The reaction mixture was diluted with DCE (20 mL), washed brine (2*10 mL), dried over Na$_2$SO$_4$, concentrated under reduced pressure. The crude product was purified by Prep-TLC (EtOAc/pet.ether=1/5) to afford Compound 7 (200 mg, 53% yield) as a light yellow oil. TLC: Pet. ether/EtOAc=1/5(v/v), Rf=0.3 $^1$H NMR (400 MHz, DMSO-d$_6$) δ 9.01 (s, 1H), 6.92 (d, J=2.6 Hz, 1H), 6.87 (d, J=2A Hz, 1H), 6.79 (d, j=2.7 Hz, 1H), 6.62 (d, j=8.1 Hz, 1H), 6.54 (dd, j=8.2, 2.1 Hz, 1H), 4.81 (s, 2H), 4.17 (q, j=7.1 Hz, 2H), 3.97

(s, 2H), 3.12 (m, 1H), 2.59-2.52 (m, 2H), 1.23-1.18 (m, 3H), 1.09 (d, J=6.9 Hz, 6H), 1.01 (t, J=7.4 Hz, 3H).

Example 8

Synthesis of 2-(3-chloro-5-ethyl-4-(4-hydroxy-3-isopropylbenzyl)phenoxy)acetic acid (Compound 8)

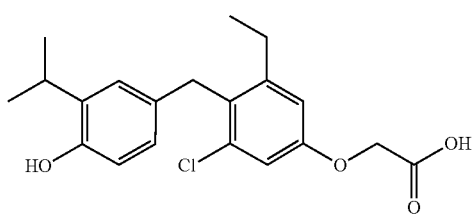

To a solution of Compound 7 (200 mg, 0.51 mmol) in THF (10 mL) was added lithium hydroxide (65 mg, 1.53 mmol) in water (0.2 mL). The mixture was stirred at rt for 2 h. The aqueous phase was acidified with HCl (2 N) to pH=3; water (2 mL) was added and the mixture was extracted with EtOAc (5 mL*3). The combined organic phase was washed with brine (15 mL), dried over $Na_2SO_4$, concentrated in vacuo and purified by Prep-HPLC (MeCN/$H_2O$) to afford Compound 8 (150 mg, 80% yield) as a colourless oil. TLC: Pet. ether/EtOAc=1/1 (v/v), Rf=0.1 LCMS: T=3.77 min, [M−1]:361.1 NMR (400 MHz, DMSO-$d_6$) δ 12.99 (s, 1H), 9.03 (s, 1H), 6.88 (d, J=2.6 Hz, 2H), 6.78 (d, J=2.7 Hz, 1H), 6.62 (d, J=8.2 Hz, 1H), 6.53 (dd, J=8.1, 2.1 Hz, 1H), 4.70 (s, 2H), 3.96 (s, 2H), 3.12 (p, J=6.9 Hz, 1H), 2.55 (t, J=7.5 Hz, 2H), 1.09 (d, J=6.9 Hz, 6H), 1.00 (t, J=7.5 Hz, 3H).

Example 9

Synthesis of 2-(3-chloro-5-ethyl-4-(4-hydroxy-3-isopropylbenzyl)phenoxy)-N,N-dimethylacetamide (Compound 9)

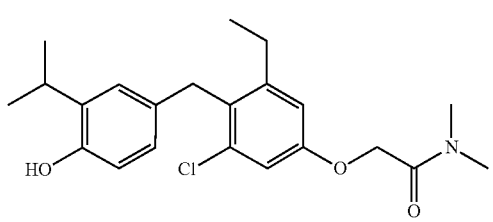

To a solution of Compound 8 (100 mg, 0.275 mmol) in DMF (5 mL) were added oxalyl dichloride (105 mg, 0.81 mmol,) and DMF (20 mg). After stirring at rt 1 h, the reaction mixture was concentrated in vacuo, the crude product was used directly. To a solution of the above acid chloride (100 mg, 0.27 mmol) in DCM (10 mL) was added N,N-dimethylamine (5 mL). After stirring at room temperature for 1 h, the mixture was poured into water (20 mL) and extracted with DCM (30 mL*3). The combined organic phase was concentrated in vacuo and purified by Prep-TLC (EtOAc/pet.ether=1/1) to afford the desired Compound 9 (50 mg, 48% yield) as a white solid. TLC: Pet. ether/EtOAc=1/1 (v/v), Rf=0.3 LCMS: T=3.85 min, [M−1]: 388.1 NMR (400 MHz, DMSO-$d_6$) δ 9.02 (s, 1H), 6.89 (dd, J=4.9, 2.4 Hz, 2H), 6.77 (d, J=2.7 Hz, 1H), 6.62 (d, J=8.2 Hz, 1H), 6.54 (d, J=2.2 Hz, 1H), 4.82 (s, 2H), 3.96 (s, 2H), 3.11 (q, J=6.9 Hz, 1H), 2.99 (s, 3H), 2.84 (s, 3H), 2.54 (t, J=7.5 Hz, 2H), 1.09 (d, J=6.9 Hz, 6H), 1.01 (t, J=7.5 Hz, 3H).

Example 10

Synthesis of ethyl 2-(4-(4-hydroxy-3-isopropylbenzyl)-3-methyl-5-(trifluoromethyl)phenoxy)acetate (Compound 10)

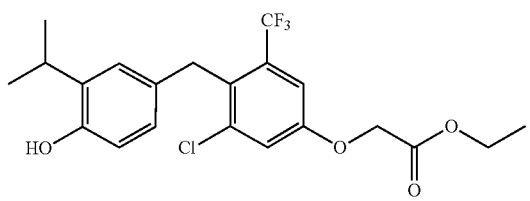

A mixture of Intermediate O (100 mg, 0.322 mmol), 2-isopropylphenol (135 mg, 0.96 mmol) and $ZnCl_2$ (1.0 M in THF, 0.8 mL) in DCE (6 mL) was stirred at 90° C. overnight. The mixture was concentrated to dryness. Water (30 mL) was added, and the mixture was extracted with DCM (25 mL*2). The combined organic phase was washed with brine (50 mL), dried over $Na_2SO_4$, and purified by reverse-phase column chromatography to afford Compound 10 (60 mg, 45% yield) as a white solid. TLC: EtOAc/pet. ether=1/5(v/v), Rf=0.39 NMR (400 MHz, DMSO-$d_6$) δ 9.04 (s, 1H), 7.13 (d, J=2.7 Hz, 1H), 7.10 (d, J=2.7 Hz, 1H), 6.79 (d, J=2.2 Hz, 1H), 6.61 (d, J=8.2 Hz, 1H), 6.40 (dd, J=8.1, 2.2 Hz, 1H), 4.88 (s, 2H), 4.18 (q, J=7.1 Hz, 2H), 3.96 (s, 2H), 3.12 (p, J=6.9 Hz, 1H), 2.10 (s, 3H), 1.20 (t, J=7.1 Hz, 4H), 1.08 (d, J=6.9 Hz, 6H).

Example 11

Synthesis of 2-(4-(4-hydroxy-3-isopropylbenzyl)-3-methyl-5-(trifluoromethyl)phenoxy)acetic acid (Compound 11)

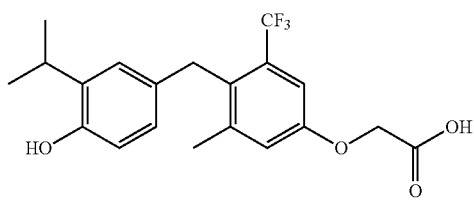

To a mixture of the Compound 10 (60 mg, 146 μmol) in methanol (3 mL) and water (1 mL) was added NaOH (18 mg, 440 μmol); the resultant solution was stirred at rt for 1 h. The mixture was acidified to pH 5-6 with 2M HCl and extracted with EtOAc (25 mL*2). The combined organic layer was washed with brine (20 mL), dried over $Na_2SO_4$, and purified by Prep-HPLC to afford Compound 11 (25 mg, 45% yield) as a light yellow solid. TLC: Pet. ether/

EtOAc=1/5(v/v), Rf=0 LCMS: T=3.79 min, [M−1]: 381.1 ¹H NMR (400 MHz, DMSO-d₆) δ 9.09 (s, 1H), 7.03 (s, 2H), 6.81 (s, 1H), 6.61 (d, J=8.2 Hz, 1H), 6.39 (dd, J=8.3, 2.2 Hz, 1H), 4.46 (s, 2H), 3.94 (s, 2H), 3.11 (q, J=6.8 Hz, 2H), 2.08 (s, 3H), 1.09 (d, J=6.9 Hz, 6H)

Example 12

Synthesis of ethyl 2-(3-bromo-4-(4-hydroxy-3-isopropylbenzyl)-5-methylphenoxy)acetate (Compound 12)

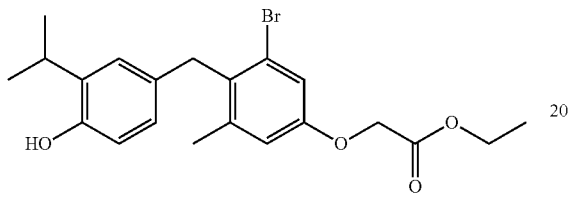

To a solution of Intermediate Q (600 mg, 1.86 mmol) in 1,2-dichloroethane (10 mL) at rt was added ZnCl₂ (634 mg, 4.65 mmol), 2-isopropylphenol (770 mg, 5.59 mmol). The mixture was heated to 85° C. overnight. The reaction was cooled to rt; DCE (10 mL) was added and the resultant mixture was washed with water (2*10 mL), then brine (2*10 mL), dried over Na₂SO₄ and concentrated under reduced pressure. The residue was purified by silica gel chromatography (pet.ether:EtOAc=100:1 to 3:1) to afford Compound 12 (400 mg, 50% yield) as a white solid. TLC: Pet. ether/EtOAc=3/1 (v/v), Rf=0.5 ¹H NMR (400 MHz, DMSO-d₆) δ 9.04 (s, 1H), 7.07 (d, J=2.6 Hz, 1H), 6.90 (d, J=2.2 Hz, 1H), 6.86-6.82 (m, 1H), 6.63 (d, J=8.2 Hz, 1H), 6.55 (dd, J=8.2, 2.2 Hz, 1H), 4.79 (s, 2H), 4.17 (q, J=7.2 Hz, 2H), 3.97 (s, 2H), 3.12 (p, J=6.8 Hz, 1H), 2.19 (s, 3H), 1.20 (t, J=7.2 Hz, 3H), 1.10 (d, J=6.8 Hz, 6H).

Example 13

Synthesis of ethyl 2-(4-(4-hydroxy-3-isopropylbenzyl)-3-methyl-5-vinylphenoxy)acetate (Compound 13)

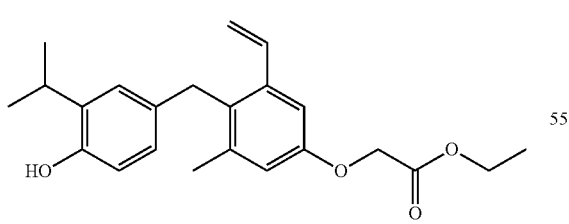

To a solution of Compound 12 (100 mg, 0.24 mmol), 4,4,5,5-tetramethyl-2-vinyl-1,3,2-dioxaborolane (55 mg, 0.36 mol) and K₃PO₄ (151 mg, 0.70 mmol) in toluene (5 mL) at rt were added tricyclohexylphosphine (13 mg, 0.04 mmol), and Palladium acetate (6 mg, 0.02 mmol). The mixture was refluxed overnight. The mixture was poured into water (10 mL) and extracted with EtOAc (10 mL*2). The combined organic phase was washed with brine (5 mL), dried over Na₂SO₄, concentrated in vacuo and purified by Prep-HPLC (MeCN/H₂O) to afford Compound 13 (20 mg, 22% yield) as a colorless oil. TLC: Pet. ether/EtOAc=5/1 (v/v), Rf=0.6 ¹H NMR (400 MHz, DMSO-d₆) δ 9.00 (s, 1H), 6.96-6.88 (m, 2H), 6.85 (d, J=2.2 Hz, 1H), 6.75 (d, J=2.8 Hz, 1H), 6.60 (d, J=8.2 Hz, 1H), 6.48 (dd, J=8.2, 2.2 Hz, 1H), 5.67 (dd, J=17.4, 1.5 Hz, 1H), 5.24 (dd, J=10.8, 1.5 Hz, 1H), 4.78 (s, 2H), 4.17 (q, J=12 Hz, 2H), 3.86 (s, 2H), 3.10 (q, j=6.8 Hz, 1H), 2.16 (s, 3H), 1.20 (d, j=12 Hz, 3H), 1.08 (d, j=6.8 Hz, 6H).

Example 14

Synthesis of 2-(4-(4-hydroxy-3-isopropylbenzyl)-3-methyl-5-vinylphenoxy)acetic acid (Compound 14)

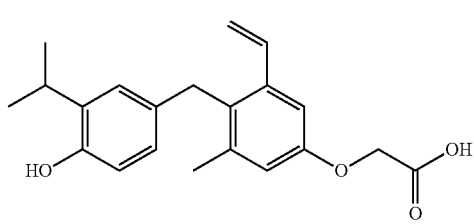

To a solution of Compound 13 in water/THF at rt may be added NaOH; the resulting mixture may be stirred at rt. The reaction may be acidified with 2N HCl, extracted with DCM, and concentrated to afford Compound 14.

Example 15

Synthesis of ethyl 2-(3-ethyl-4-(4-hydroxy-3-isopropylbenzyl)-5-methylphenoxy)acetate (Compound 15)

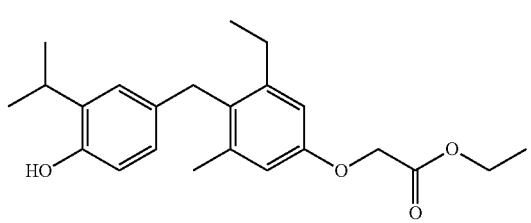

To a solution of Compound 13 (10 mg, 0.02 mmol) in THF (5 mL) was added Pd/C (15 mg). The mixture was stirred at rt for 16 h under 1 atm H₂ atmosphere. The mixture was filtered through Celite to remove catalyst and concentrated in vacuo to afford Compound 15 (8 mg, 79% yield) as a white solid. TEC: Pet.ether/EtOAc=5/1(v/v), Rf=0.6 LCMS:T=4.306 min, [M+23]:393.0.

Example 16

Synthesis of 2-(3-ethyl-4-(4-hydroxy-3-isopropyl-benzyl)-5-methylphenoxy)acetic acid (Compound 16)

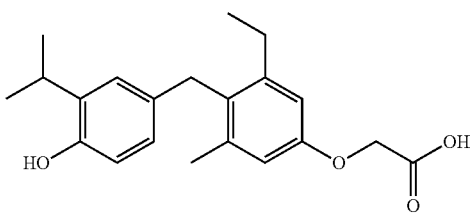

To a solution of Compound 15 (8 mg, 0.02 mmol) in THF (5 mL), LiOH·H$_2$O (3 mg, 0.06 mmol) in water (0.2 mL) was added; the mixture was stirred at rt for 30 min. Water (5 mL) was added, the mixture was acidified to pH=6-7 with 2N HCl, and extracted with EtOAc (10 mL*2). The combined organic phase was washed by brine (20 mL), dried over Na$_2$SO$_4$, concentrated in vacuo and purified by Prep-HPLC (MeCN/H$_2$O) to afford Compound 16 (4 mg, 54% yield) as a colorless oil. TLC: Pet. ether/EtOAc=1/1(v/v), Rf=0.1 LCMS: 1=3.736 min, [M−1]:341.2 $^1$H NMR (400 MHz, DMSO-d$_6$) δ 12.91 (s, 1H), 8.96 (s, 1H), 6.83 (d, J=2.2 Hz, 1H), 6.63-6.58 (m, 3H), 6.44 (dd, J=8.2, 2.2 Hz, 1H), 4.61 (s, 2H), 3.81 (s, 2H), 3.12 (p, j=6.8 Hz, 1H), 2.51-2.50 (q, j=7.4 Hz, 2H), 2.13 (s, 3H), 1.09 (d, J=6.8 Hz, 6H), 1.02 (d, J=7.4 Hz, 3H).

Example 17

Synthesis of ethyl 2-(3-chloro-4-(4-hydroxy-3-isopropylbenzyl)-5-(trifluoromethyl)phenoxy)acetate (Compound 17)

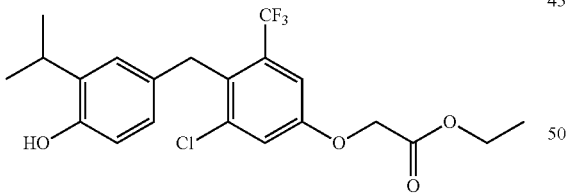

To a solution of Intermediate T (0.31 g, 940 μmol) in DCE (3 mL) at rt was added zinc chloride in THF (1.0M, 1.87 mmol, 1.87 mL) and 2-isopropylphenol (383 mg, 2.8 mmol). The mixture was heated to 85° C. overnight, diluted with water (5 mL), extracted with EtOAc (3 mL*3). The combined organic phase was washed with brine (5 mL), dried over Na$_2$SO$_4$, and concentrated under reduced pressure. The crude product was purified by Prep-TLC (PE/EtOAc=5/1) to afford Compound 17 (260 mg, 603 μmol, 64% yield) as a colorless oil. TLC: EtOAc/pet. ether=1/5(v/v), R$_f$=0.35 $^1$H NMR (400 MHz, DMSO-d$_6$) δ 9.04 (s, 1H), 7.47 (d, j=2.7 Hz, 1H), 7.31 (d, j=2.7 Hz, 1H), 6.79 (d, J=2.2 Hz, 1H), 6.62 (d, j=8.2 Hz, 1H), 6.44 (dd, J=8.2, 2.3 Hz, 1H), 4.97 (s, 2H), 4.18 (q, 7=7.1 Hz, 2H), 4.07 (s, 2H), 3.12 (p, 7=6.9 Hz, 1H), 1.21 (t, 7=6.3 Hz, 3H), 1.08 (d, 7=6.9 Hz, 6H).

Example 18

Synthesis of 2-(3-chloro-4-(4-hydroxy-3-isopropyl-benzyl)-5-(trifluoromethyl)phenoxy)acetic acid (Compound 18)

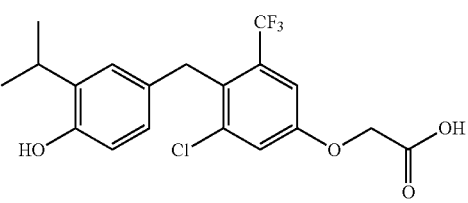

To a solution of Compound 17 (0.26 g, 603 μmol) in THF/H$_2$O (3/2 mL) at rt was added LiOH (38.0 mg, 905 μmol). The mixture was stirred at rt 2 h, diluted with water (10 mL), acidified with 1 N HCl to pH=5-6, extracted with EtOAc (3 mL*3). The combined organic phase was washed by brine (5 mL), dried over Na$_2$SO$_4$, concentrated under reduce pressure. The crude product was purified by Prep-HPLC (MeCN/water range from 10/90 to 70/30) to afford Compound 18 (80 mg, 200 μmol, 32.9% yield) as an off-white solid. TLC: MeOH/DCM=1/10(v/v), Rf=0.25 LCMS: T=1.976 min, [M−1]:401.1 $^1$H NMR (400 MHz, DMSO-d$_6$) δ 9.05 (s, 1H), 7.43 (d, J=2.7 Hz, 1H), 7.28 (d, J=2.7 Hz, 1H), 6.81 (d, J=2.2 Hz, 1H), 6.62 (d, J=8.2 Hz, 1H), 6.44 (dd, J=8.3, 2.2 Hz, 1H), 4.85 (s, 2H), 4.07 (s, 2H), 3.12 (m, 1H), 1.08 (d, J=6.9 Hz, 6H).

Example 19

Synthesis of ethyl 2-(4-(4-hydroxy-3-isopropylbenzyl)-3-methyl-5-(prop-1-en-2-yl)phenoxy)acetate (Compound 19)

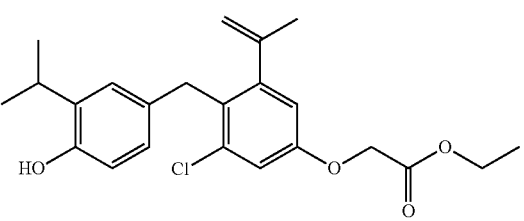

To a solution of Compound 12 (300 mg, 712 μmol) in 1,4-dioxane (10 mL) at rt was added potassium isopropenyltrifluoroborate (211 mg, 1.42 mmol), Cs$_2$CO$_3$ (464 mg, 1.42 mmol) and Pd(dppf)Cl$_2$ (58.2 mg, 71.20 μmol) under a blanket of dry nitrogen gas. The reaction was microwaved with stirring at 120° C. for 1 h. The reaction mixture was diluted with EtOAc (20 mL), washed with brine (5 mL), dried over Na$_2$SO$_4$, and concentrated under reduced pressure. The crude product was purified by Prep-HPLC to afford Compound 19 (120 mg, 44% yield) as a yellow oil. TLC: EtOAc/pet. ether=1/5(v/v), Rf=0.35 NMR (400 MHz, DMSO-d$_6$) δ 8.95 (s, 1H), 6.75 (d, J=2.2 Hz, 1H), 6.69 (d, J=2.8 Hz, 1H), 6.59 (s, 1H), 6.52 (d, J=2.8 Hz, 1H), 6.48 (dd, J=8.2, 2.3 Hz, 1H), 5.11-5.07 (m, 1H), 4.74 (s, 2H), 4.70 (dd, 7=2.4, 1.1 Hz, 1H), 4.17 (d, J=7.1 Hz, 2H), 3.81 (s, 2H), 3.18-3.06 (m, 1H), 2.06 (s, 3H), 1.87 (d, J=1.2 Hz, 3H), 1.19 (t, 3H), 1.07 (d, J=6.9 Hz, 6H).

Example 20

Synthesis of 2-(4-(4-hydroxy-3-isopropylbenzyl)-3-methyl-5-(prop-1-en-2-yl)phenoxy)acetic acid (Compound 20)

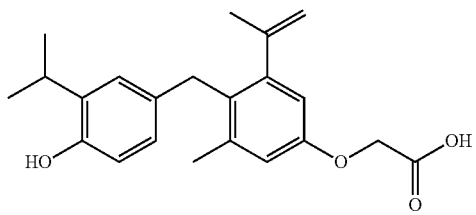

20

To a solution of Compound 19 (120 mg, 314 μmol) in water (5 mL)/THF (1 mL) at rt was added NaOH (37.65 mg, 941.20 μmol); the resulting mixture was stirred at rt for 1 h. The reaction was acidified to pH=6-7 with 2N HCl, extracted with DCM (30 mL×3), and concentrated to afford Compound 20 (110 mg, 98% yield). TLC: Pet. ether/EtOAc=1/5(v/v), Rf=0 LCMS: T=3.799 min, [M−1]: 353.2 $^1$H NMR (400 MHz, DMSO-d$_6$) δ 13.02 (s, 1H), 8.95 (s, 1H), 6.77 (d, J=2.2 Hz, 1H), 6.67 (d, J=2.8 Hz, 1H), 6.61 (d, j=8.1 Hz, 1H), 6.52-6.45 (m, 2H), 5.08 (t, j=2.0 Hz, 1H), 4.71 (dd, J=2.3, 1.1 Hz, 1H), 4.61 (s, 2H), 3.81 (s, 2H), 3.15-3.07 (m, 1H), 2.06 (s, 3H), 1.87 (s, 3H), 1.07 (d, j=6.9 Hz, 6H).

Example 21

Synthesis of 2-(4-(4-hydroxy-3-isopropylbenzyl)-3-isopropyl-5-methylphenoxy)acetic acid (Compound 21)

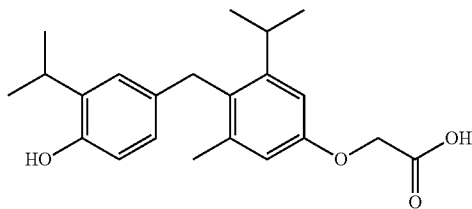

21

To a solution of Compound 20 (50 mg, 141 μmol) in methanol (5 mL) at rt was added Pd/C (5 mg), the resulting mixture was stirred under a blanket of hydrogen gas at 70° C. for 16 h. The reaction was purged with nitrogen, filtered, concentrated and purified by Prep-HPLC to afford Compound 21 (15 mg, 29% yield). TLC: DCM/MeOH=20/1(v/v), Rf=0.35 LCMS: T=2.010 min, [M−1]:355.2 $^1$H NMR (400 MHz, DMSO-d$_6$) δ 12.91 (s, 1H), 8.97 (s, 1H), 6.78 (d, J=2.1 Hz, 1H), 6.68 (d, J=2.7 Hz, 1H), 6.64-6.56 (m, 2H), 6.49 (dd, J=8.2, 2.1 Hz, 1H), 4.62 (s, 2H), 3.84 (s, 2H), 3.08 (dp, J=33.6, 6.9 Hz, 2H), 2.14 (s, 3H), 1.07 (dd, J=6.9, 4.1 Hz, 12H).

Example 22

Synthesis of (E)-ethyl 2-(4-(4-hydroxy-3-isopropylbenzyl)-3-methyl-5-(prop-1-enyl)phenoxy)acetate (Compound 22)

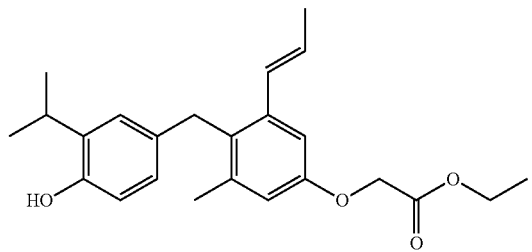

22

To a solution of Compound 12 (100 mg, 0.24 mmol), 4,4,5,5-tetramethyl-2-1-propenyl-1,3,2-dioxaborolane (100 mg, 0.60 mmol) and K$_3$PO$_4$ (151 mg, 0.70 mol) in toluene (10 mL) at rt was added palladium acetate (6 mg, 0.02 mmol), and tricyclohexylphosphine (13 mg, 0.04 mmol). The mixture was refluxed overnight. The mixture was poured into water (10 mL) and extracted with EtOAc (10 mL*2). The combined organic phase was washed with brine (5 mL), dried over Na$_2$SO$_4$, concentrated in vacuo and purified by Prep-HPLC (MeCN/H$_2$O) to afford Compound 22 (60 mg, 68% yield) as a white solid. TLC: Pet. ether/EtOAc=5/1 (v/v), Rf=0.6.

Example 23

Synthesis of (E)-2-(4-(4-hydroxy-3-isopropylbenzyl)-3-methyl-5-(prop-1-enyl)phenoxy)acetic acid (Compound 23)

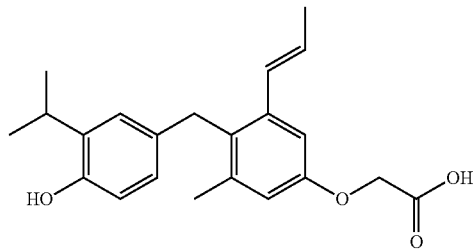

23

To a solution of Compound 22 (50 mg, 0.13 mmol) in THF (5 mL), LiOH·H$_2$O (10 mg, 0.39 mmol) in water (0.2 mL) was added; the mixture was stirred at rt for 1 h. Water (5 mL) was added, the pH was adjusted to pH=3 with HCl (1N), and the mixture was extracted with EtOAc (10 mL*2). The combined organic phase was washed by brine (20 mL), dried over Na$_2$SO$_4$, concentrated in vacuum and purified by Prep-HPLC (MeCN/H$_2$O) to afford Compound 23 (25 mg, 53% yield) as a white solid. TLC: Pet. ether/EtOAc=1/1(v/v), Rf=0.1 LCMS: T=3.726 min, [M−1]:353.1 $^1$H NMR (400 MHz, DMSO-d$_6$) δ 8.98 (s, 1H), 6.89 (d, J=2.2 Hz, 1H), 6.81 (d, J=2.8 Hz, 1H), 6.65-6.57 (m, 3H), 6.48 (dd, J=8.2, 2.2 Hz, 1H), 6.08 (dd, J=15.4, 6.7 Hz, 1H), 4.58 (s, 2H), 3.82 (s, 2H), 3.11 (m, 1H), 2.14 (s, 3H), 1.79 (dd, 7=6.6, 1.6 Hz, 3H), 1.09 (d, J=6.8 Hz, 6H).

Example 24

Synthesis of ethyl 2-(4-(4-hydroxy-3-isopropylbenzyl)-3-methyl-5-propylphenoxy)acetate (Compound 24)

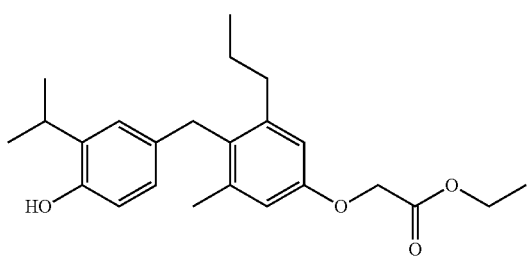

24

To a solution of Compound 22 (60 mg, 0.15 mmol) in THF (10 mL) and was added Pd/C (50 mg). The mixture was stirred at 30° C. for 16 h under 1 atm H$_2$ atmosphere. The mixture was filtered through Celite to remove catalyst and concentrated in vacuo to afford Compound 24 (60 mg, 99% yield) as a white solid. TLC: Pet. ether/EtOAc=5/1(v/v), Rf=0.6 LCMS: T=4.420 min, [M−1]:383.2.

Example 25

Synthesis of 2-(4-(4-hydroxy-3-isopropylbenzyl)-3-methyl-5-propylphenoxy)acetic acid (Compound 25)

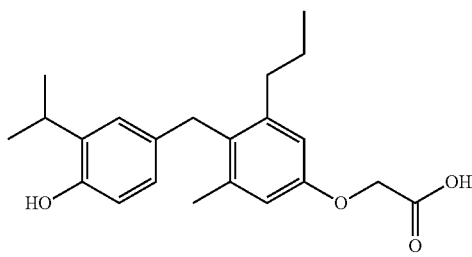

25

To a solution of compound 24 (60 mg, 0.15 mmol) in THF (8 mL), LiOH·H$_2$O (19 mg, 0.45 mmol) in water (0.2 mL) was added; the mixture was stirred at rt for 30 min. Water (5 mL) was added, pH was adjusted to pH=3 with HCl (1 N), and the mixture was extracted with EtOAc (10 mL*2). The combined organic phase was washed with brine (20 mL), dried over Na$_2$SO$_4$, concentrated in vacuum and purified by Prep-HPLC (MeCN/H$_2$O) to afford Compound 25 (20 mg, 35% yield) as a colorless oil. TLC: Pet. ether/EtOAc=1/1 (v/v), Rf=0.1 LCMS: T=3.897 min, [M−1]:355.2 $^1$H NMR (400 MHz, DMSO-d$_6$) δ 12.99 (s, 1H), 8.97 (s, 1H), 6.82 (d, J=2.2 Hz, 1H), 6.63-6.54 (m, 3H), 6.48-6.42 (m, 1H), 4.59 (s, 2H), 3.81 (s, 2H), 3.12 (p, J=6.8 Hz, 1H), 2.46 (t, J=7.8 Hz, 2H), 2.12 (s, 3H), 1.40 (q, J=7.6 Hz, 2H), 1.09 (d, J=6.8 Hz, 6H), 0.83 (t, J=7.2 Hz, 3H).

Example 26

Synthesis of ethyl 2-(3-cyclopropyl-4-(4-hydroxy-3-isopropylbenzyl)-5-methylphenoxy)acetate (Compound 26)

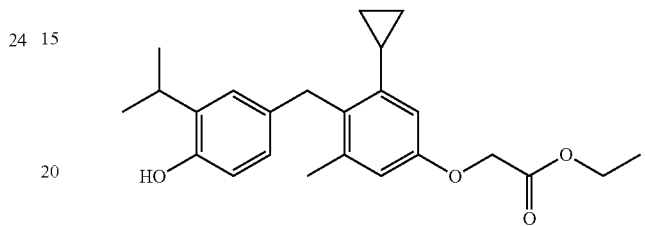

26

To a solution of Compound 12 (50 mg, 0.12 mmol), cyclopropylboronic acid (15 mg, 0.18 mmol) and K$_3$PO$_4$ (75 mg, 0.35 mmol) in toluene (8 mL) at rt was added tricyclohexylphosphine (7 mg, 0.02 mmol) palladium acetate (3 mg, 0.01 mmol). The mixture was refluxed overnight. The mixture was poured into water (10 mL) and extracted with EtOAc (10 mL*2). The combined organic phase was washed with brine (5 mL), dried over Na$_2$SO$_4$, concentrated in vacuum and purified by Prep-HPLC (MeCN/H$_2$O) to afford Compound 26 (10 mg, 21% yield) as a colorless solid. TLC: Pet. ether/EtOAc=5/1 (v/v), Rf=0.2.

Example 27

Synthesis of 2-(3-cyclopropyl-4-(4-hydroxy-3-isopropylbenzyl)-5-methyl phenoxyacetic acid (Compound 27)

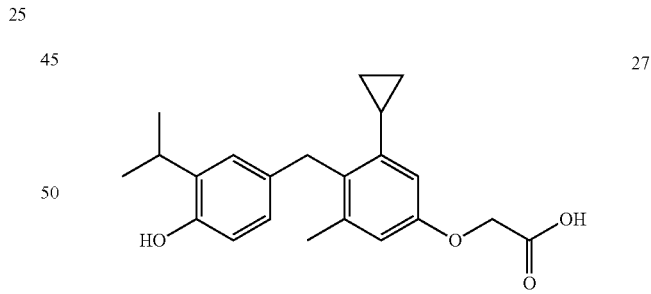

27

To a solution of compound 26 (10 mg, 0.02 mmol) in THF (5 mL), LiOH·H$_2$O (3 mg, 0.06 mmol) in water (0.5 mL) was added. The mixture was stirred at rt 1 h. Water (5 mL) was added; the reaction was acidified to pH=6-7 with 2N HCl, then extracted with EtOAc (5 mL*3). The combined organic phase was washed by brine (15 mL), dried over Na$_2$SO$_4$, concentrated in vacuum and purified by Prep-TLC (DCM/MeOH=10:1) to afford Compound 27 (4 mg, 43% yield) as a colorless oil. TLC: Pet. ether/EtOAc=1/1 (v/v), Rf=0.1 LCMS: T=3.698 min, [M−1]:353.1 $^1$H NMR (400 MHz, DMSO-d$_6$) δ 9.05 (s, 1H), 6.88 (s, 1H), 6.61 (d, J=8.2 Hz, 1H), 6.51 (d, J=7.8 Hz, 2H), 6.31 (s, 1H), 4.17 (s, 2H), 3.97 (s, 2H), 3.11 (q, J=7.0 Hz, 1H), 2.11 (s, 3H), 1.81 (m, 1H), 1.09 (d, J=6.8 Hz, 6H), 0.78 (d, J=8.2 Hz, 2H), 0.51 (d, J=5.4 Hz, 2H).

Example 28

Synthesis of ethyl 2-(3-bromo-5-chloro-4-(4-hydroxy-3-isopropylbenzyl)phenoxy)acetate (Compound 28)

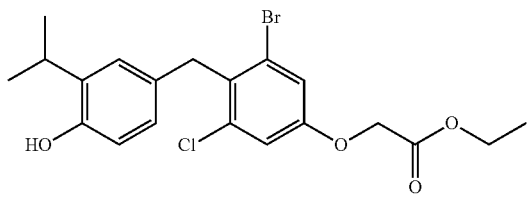

28

A mixture of Intermediate W (1.0 g, 2.9 mmol), 2-isopropylphenol (1.19 g, 8.8 mmol) and $ZnCl_2$ (1 M in THF, 7.3 mL) in DCE (20 mL) was stirred at 90° C. overnight. The mixture was concentrated to dryness. $H_2O$ (30 mL) was added, the mixture was extracted with EtOAc (25 mL*2). The combined organic phase was washed with brine (50 mL), dried over $Na_2SO_4$, and purified by reverse-phase column chromatography to afford Compound 28 (500 mg, 39% yield) as a white solid. TLC: EtOAc/pet. ether=1/5(v/v), Rf=0.39 NMR (400 MHz, DMSO-$d_6$) δ 9.09 (s, 1H), 7.28 (d, J=2.8 Hz, 1H), 7.17 (d, J=2.4 Hz, 1H), 6.96 (s, 1H), 6.68-6.61 (m, 2H), 4.88 (s, 2H), 4.17 (q, J=7.2 Hz, 2H), 4.08 (s, 2H), 3.16-3.09 (m, 1H), 1.20 (t, J=7.2 Hz, 3H), 1.10 (d, J=6.8 Hz, 6H).

Example 29

Synthesis of ethyl 2-(3-chloro-4-(4-hydroxy-3-isopropylbenzyl)-5-(prop-1-en-2-yl)phenoxy)acetate (Compound 29)

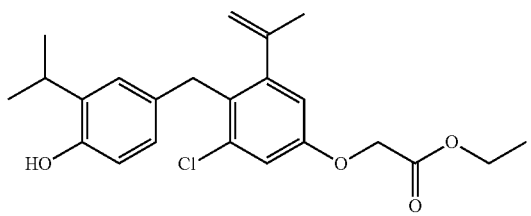

29

A mixture of Compound 28 (80 mg, 180 μmol), potassium isopropenyltrifluoroborate (54 mg, 360 μmol), Pd(dppf)Cl$_2$ (13.3 mg, 18 μmol) and Cs$_2$CO$_3$ (120 mg, 360 μmol) in 1,4-dioxane (3 mL) and water (0.3 mL) was reacted at 120° C. for 2 h in a microwave reactor. The mixture was concentrated to dryness. H$_2$O (30 mL) was added, and the mixture was extracted with EtOAc (25 mL*2). The combined organic phase was washed with brine (50 mL), dried over Na$_2$SO$_4$, and purified by silica gel column chromatography (pet. ether to Pet. ether/EtOAc=10/1) to afford Compound 29 (60 mg, 82% yield) as a colorless oil. TLC: EtOAc/pet. ether=1/5(v/v), Rf=0.39 $^1$H NMR (400 MHz, DMSO-$d_6$) δ 9.01 (s, 1H), 7.00 (d, J=2.8 Hz, 1H), 6.78 (d, J=2.4 Hz, 1H), 6.71 (d, J=2.8 Hz, 1H), 6.61 (d, J=8.4 Hz, 1H), 6.54 (dd, J=8.4, 2.4 Hz, 1H), 5.14 (t, 7=1.8 Hz, 1H), 4.83 (s, 2H), 4.73-4.72 (m, 1H), 4.17 (q, J=12 Hz, 2H), 3.92 (s, 2H), 3.15-3.08 (m, 1H), 1.83 (s, 3H), 1.22-1.18 (m, 6H), 1.07 (d, 7=6.8 Hz, 6H).

Example 30

Synthesis of 2-(3-chloro-4-(4-hydroxy-3-isopropylbenzyl)-5-(prop-1-en-2-yl)phenoxy)acetic acid (Compound 30)

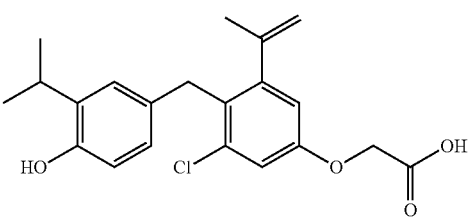

30

A mixture of Compound 29 (60 mg, 150 μmol) and NaOH (18 mg, 450 μmol) in Methanol (3 mL) and water (1 mL) was stirred at rt for 1 h. The mixture was acidified to pH 5-6 with 2M HCl. Water (30 mL) was added, and the mixture was extracted with EtOAc (25 mL*2). The combined organic phase was washed with brine (20 mL), dried over Na$_2$SO$_4$, and purified by Prep-HPLC to afford Compound 30 (25 mg, 45% yield) as a white solid. TLC: Pet. ether/EtOAc=1/5(v/v), Rf=0 LCMS: T=2.013 min, [M−1]:373.1 NMR (400 MHz, DMSO-$d_6$) δ 9.01 (s, 1H), 6.96 (d, J=2.8 Hz, 1H), 6.79 (d, J=2.0 Hz, 1H), 6.69 (d, J=2.8 Hz, 1H), 6.61 (d, J=8.4 Hz, 1H), 6.53 (dd, J=8.4, 2.0 Hz, 1H), 5.16-5.12 (m, 1H), 4.72 (s, 3H), 3.92 (s, 2H), 3.12 (p, J=6.8 Hz, 1H), 1.83 (s, 3H), 1.08 (d, J=6.8 Hz, 6H).

Example 31

Synthesis of 2-(3-chloro-4-(4-hydroxy-3-isopropylbenzyl)-5-isopropylphenoxy)acetic acid (Compound 31)

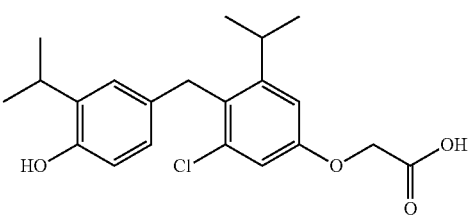

31

To a solution of Compound 30 (100 mg, 266 μmol) in methanol (5 mL) at rt was added Pd/C (10 mg); the resulting mixture was stirred at 70° C. overnight under a blanket of hydrogen gas. The reaction mixture was purged with nitrogen, the solution was filtered, concentrated and purified by Prep-HPLC to afford Compound 31(15 mg, 15% yield). TLC: DCM/MeOH=10/1 (v/v), Rf=0.35 LCMS: T=2.133 min, [M−1]: 375.1 $^1$H NMR (400 MHz, DMSO-$d_6$) δ 13.00

(s, 1H), 9.02 (s, 1H), 6.86 (d, J=2.8 Hz, 1H), 6.84-6.82 (m, 2H), 6.63 (d, J=8.4 Hz, 1H), 6.57-6.55 (m, 1H), 4.69 (s, 2H), 4.00 (s, 2H), 3.14-3.10 (m, 1H), 3.09-3.05 (m, 1H), 1.08 (d, J=6.8 Hz, 6H), 1.04 (d, J 15=6.8 Hz, 6H).

Example 32

Synthesis of 2-(3-chloro-4-(4-hydroxy-3-isopropyl-benzyl)-5-(prop-1-en-2-yl)phenoxy)acetyl chloride (Compound 32)

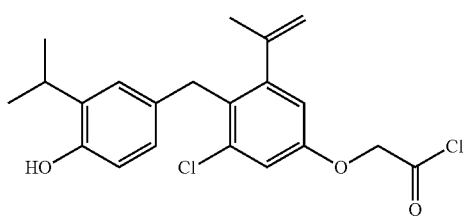

32

A mixture of Compound 30 (180 mg, 480 umol) and oxalyl chloride (61 mg, 480 umol) in DCM (5 mL) was stirred at 0° C. for 2 h. The mixture was concentrated to dryness to afford crude Compound 32 (180 mg, 95% yield) as a colorless oil which was used as is.

Example 33

Synthesis of 2-(3-chloro-4-(4-hydroxy-3-isopropyl-benzyl)-5-(prop-1-en-2-yl)phenoxy)-N-methylacetamide (Compound 33)

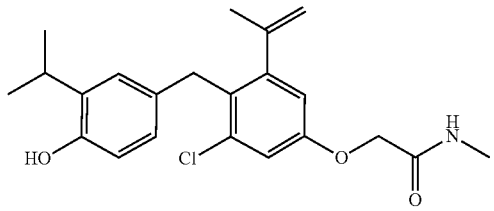

33

A solution of Compound 32 (180 mg, 458 umol) in methylamine (2M/THF, 1 mL) and THF (5 mL) was stirred at RT for 5 min. Water (20 mL) was added; the mixture was extracted with EtOAc (15 mL*2). The combined organic layer was washed with water (20 mL*2), then brine (20 mL), dried over Na$_2$SO$_4$, and purified by Prep-HPLC (DCM/MeOH=20/1) to afford Compound 32 (80 mg, 45% yield) as a white solid. TLC: DCM/MeOH=20/1(v/v), Rf=0.40 LCMS: RT=2.118 min, [M+1]:388.2 NMR (400 MHz, DMSO-d$_6$) δ 8.99 (s, 1H), 8.05 (d, J=5.2 Hz, 1H), 7.02 (d, J=2.8 Hz, 1H), 6.79 (d, J=2.0 Hz, 1H), 6.76 (d, J=2.4 Hz, 1H), 6.61 (d, J=8.4 Hz, 1H), 6.54 (dd, J=8.4, 2.4 Hz, 1H), 5.15 (s, 1H), 4.74 (s, 1H), 4.49 (s, 2H), 3.93 (s, 2H), 3.12 (p, J=6.8 Hz, 1H), 2.65 (d, J=4.8 Hz, 3H), 1.84 (s, 3H), 1.08 (d, J=6.8 Hz, 6H).

Example 34

Synthesis of 2-(3-chloro-4-(4-hydroxy-3-isopropyl-benzyl)-5-(prop-1-en-2-yl)phenoxy)-N,N-dimethyl-acetamide (Compound 34)

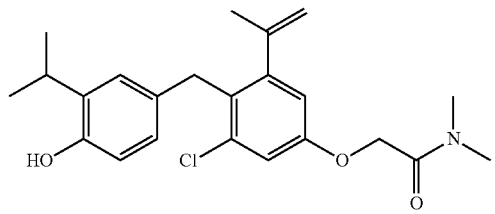

34

A mixture of Compound 32 (180 mg, 458 umol) in dimethylamine (2.0 M in THF/2 mL) was stirred at RT for 5 min. Water (30 mL) was added; the mixture was extracted with EtOAc (15 mL*2). The combined organic layer was washed with brine (20 mL), dried over Na$_2$SO$_4$, and purified by Prep-HPLC to afford Compound 34 (75 mg, 41% yield) as a white solid. TLC: DCM/MeOH=20/1 (v/v), Rf=0.4 LCMS: RT=2.261 min, [M+1]:402.2 $^1$H NMR (400 MHz, DMSO-d$_6$) δ 8.99 (s, 1H), 6.96 (d, J=2.6 Hz, 1H), 6.80 (d, j=2.1 Hz, 1H), 6.69 (d, j=2.7 Hz, 1H), 6.61 (d, j=8.2 Hz, 1H), 6.54 (dd, j=8.2, 2.2 Hz, 1H), 5.14 (s, 1H), 4.84 (s, 2H), 4.73 (s, 1H), 3.92 (s, 2H), 3.12 (p, J=6.8 Hz, 1H), 2.98 (s, 3H), 2.84 (s, 3H), 1.83 (s, 3H), 1.08 (d, J=6.9 Hz, 6H).

Example 35

Synthesis of 2-(3-chloro-4-(4-hydroxy-3-isopropyl-benzyl)-5-isopropylphenoxy)-A-methylacetamide (Compound 35)

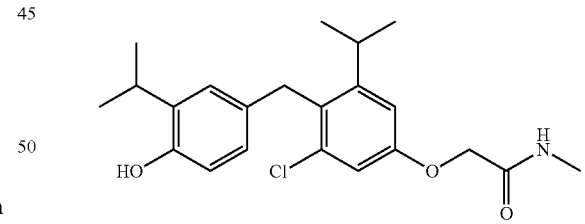

35

A mixture of Compound 33 (60 mg, 155 umol) and Raney Ni (60 mg) in THF (3 mL) was stirred under H$_2$ atmosphere (1 atm) at 55° C. overnight. The mixture was filtered, concentrated to dryness, and purified by Prep-HPLC to afford Compound (7 mg, 11% yield) as a white solid. TLC: DCM/MeOH=20/1 (v/v), Rf=0.38 LCMS: RT=2.198 min, [M−1]:388.2 $^1$H NMR (400 MHz, DMSO-d$_6$) δ 9.02 (s, 1H), 8.07 (d, J=5.4 Hz, 1H), 6.94-6.90 (m, 2H), 6.82 (d, j=2.1 Hz, 1H), 6.63 (d, j=8.2 Hz, 1H), 6.57 (dd, j=8.2, 2.2 Hz, 1H), 4.48 (s, 2H), 4.01 (s, 2H), 3.15-3.04 (m, 2H), 2.66 (d, J 5=4.7 Hz, 3H), 1.06 (dd, j=12.6, 6.8 Hz, 12H).

Example 36

Synthesis of 2-(3-chloro-4-(4-hydroxy-3-isopropylbenzyl)-5-isopropylphenoxy)-N,N-dimethylacetamide (Compound 36)

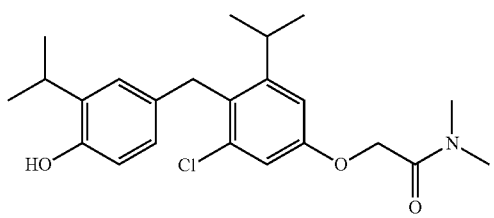

A mixture of Compound 34 (45 mg, 111.96 umol) and Raney Ni (45 mg) in THF (3 mL) was stirred under $H_2$ atmosphere (1 atm) at 55° C. overnight. The mixture was filtered, concentrated to dryness, and purified by Prep-HPLC to afford Compound 36 (15 mg, 33% yield) as a white solid. TLC: DCM/MeOH=20/1 (v/v), Rf=0.38 LCMS: RT=2.338 min, [M+1]:404.1 NMR (400 MHz, DMSO-$d_6$) δ 9.02 (s, 1H), 6.88 (d, j=2.6 Hz, 1H), 6.84-6.82 (m, 2H), 6.63 (d, j=8.2 Hz, 1H), 6.56 (dd, j=8.2, 2.2 Hz, 1H), 4.82 (s, 2H), 4.00 (s, 2H), 3.16-3.03 (m, 2H), 3.00 (s, 3H), 2.85 (s, 3H), 1.08 (d, j=7.0 Hz, 6H), 1.04 (d, j=6.8 Hz, 6H).

Compounds of the present invention demonstrate novel and unanticipated activity, both in vitro and in vivo, as demonstrated in the Examples below.

Example 32

Thyroid-Hormone Reporter-Gene Assays

Compounds 2 and 5 were tested for thyroid-hormone receptor (TR) activity using TR reporter-gene assays. Reporter cells used in the assays express a TR-receptor hybrid (either TRα or TRP) in which the native N-terminal DNA binding domain (DBD) has been replaced with that of the yeast Gal4 DBD. The reporter gene, firefly luciferase, is functionally linked to the Gal4 upstream activation sequence (UAS). Both cell lines were derived from human embryonic kidney (HEK293).

Step 1: A suspension of reporter cells was prepared in cell recovery medium containing 10% charcoal-stripped FBS, and dispensed into assay plates. The plates were pre-incubated for 6 hours in a cell culture incubator (37° C./5% $CO2$/85% humidity).

Step 2: Test compound master stocks and triiodothyronine were diluted in DMSO to generate solutions at "1,000×-concentration" relative to each final treatment concentration. These Intermediate Stocks were subsequently diluted directly into compound screening medium containing 10% charcoal-stripped FBS to generate "2×-concentration" treatment media (containing 0.2, 0.4 or 0.8% DMSO).

Step 3: At the end of the pre-incubation period, culture media were discarded from the assay plates, and all wells received 100 μl of compound screening medium. 100 μl of each of the previously prepared "2×-concentration" treatment media were dispensed into duplicate assay wells, thereby achieving the desired final treatment concentrations. The final concentration of DMSO in all assay wells was 0.1, 0.2 or 0.4%. Assay plates were incubated for 24 hr in a cell culture incubator (37° C./5% CO2/85% humidity).

Step 4: At the 24 h assay endpoint, treatment media were discarded and 100 μl/well of luciferase detection reagent was added. Relative luminometer units (RLUs) were quantified from each assay well. The performance of the TRα and TRβ assays was validated using the reference agonist triiodothyronine (T3).

The results of these assays are presented in Table 2 below, wherein data are reported as EC50 values determined for TRα and TRβ receptors, with compounds grouped according to their potency as follows:

Potency coding: +$EC_{50}$>1,000 nM

++100 nM<$EC_{50}$≤1,000 nM

+++10 nM<$EC_{50}$≤100 nM

++++$EC_{50}$≤10 nM

Additionally for each agonist in Table 2 there is recorded a "T3-benchmarked selectivity index" (T3-SI) calculated as $EC_{50}$ (TRα)*T3-$EC_{50}$ (TRβ)/$EC_{50}$ (TRβ)*T3-$EC_{50}$ (TRα), where T3-$EC_{50}$ (TRα) and T3-$EC_{50}$ (TRβ) are the values recorded for the internal standard T3 in the same experiment. Compounds are grouped according to their selectivity as follows:

Selectivity coding: +T3-SI≤3×

++3×<T3-SI≤30×

+++T3-SI>30×

As indicated by the data in Table 2, compounds of the present invention show improved TRβ selectivity when compared to the natural agonist T3.

TABLE 2

| Compound | TRα | TRβ | T3-SI |
|---|---|---|---|
| T3 | ++++ | +++ | + |
| 2 | ++ | ++ | ++ |
| 5 | +++ | +++ | ++ |
| 8 | ++ | +++ | ++ |
| 11 | ++ | +++ | ++ |
| 16 | ++ | +++ | ++ |
| 18 | +++ | +++ | ++ |
| 20 | ++ | +++ | ++ |
| 21 | +++ | +++ | ++ |
| 23 | + | ++ | ++ |
| 25 | ++ | ++ | ++ |
| 27 | + | ++ | ++ |
| 30 | ++ | +++ | ++ |
| 31 | +++ | ++++ | ++ |

FIG. 1 shows a detailed view of an X-ray crystal structure of Sobetirome bound to the TRβ receptor (PDB 3IMY), focusing on the binding pocket. While the highlighted binding pockets (corresponding to docking sites for $X^1$ and $X^2$) are clearly non-identical, the majority of TR ligands have $X^1=X^2$. A non-symmetrical distribution of $X^1$ and $X^2$ might allow for simultaneous optimization of both binding sites, leading to improvements in potency. And because there is rotational freedom around the bonds connecting the proximal aryl group to the rest of the ligand, each $X^1$ and $X^2$ can "choose" the binding site that it prefers.

The results of TR screening for Compound 5 (Table 2) support this premise. Sobetirome, with Me groups at $X^1$ and $X^2$, has a functional EC50 (TRβ) of 68 nM. The di-bromo analog of Sobetirome ($X^1=X^2$=Br) has a functional $EC_{50}$ (TRβ) of 10 nM, suggesting that bromine is a superior substituent at these sites when compared to methyl. Unexpectedly, Compound 5 is equipotent with the di-bromo analog, indicating that the benefit of Me>Br substitution comes at one of the two binding sites.

Example 33

In Vivo Activity

Animal Studies

Compounds of the current invention may be tested for thyroid-hormone receptor agonist activity in an in vivo model according to the following protocol.

Male Sprague-Dawley rats (6 weeks old) are placed on a high cholesterol chow (HC Chow; 1.5% Cholesterol, 0.5% choline) for at least 10 days. Animals are weighed on Day −1. Test compounds are formulated in 1% NMP/1% Solutol and dosed orally (PO), subcutaneously (SC) or intraperitoneally (IP) for 7 days, with each daily dose based on the body weight on that day. On Day 1 and Day 7, approximately 24 hrs after the first and last dose, respectively, blood samples are obtained via the saphenous vein, processed for serum and frozen at −80° C. Serum samples are analyzed for total cholesterol, LDL cholesterol and/or triglycerides using a clinical chemistry analyzer. If desired, test compound levels may be determined in these same samples by LCMS, comparing peak area to authentic standards. The rats are then anesthetized with isoflurane and an additional blood sample collected from the inferior vena cava or via cardiac puncture. Samples were again processed for serum, then analyzed for T3/T4/TSH levels by ELISA. Rats are terminated by exsanguination or pneumothorax; organs are harvested and weighed. Organ weight data are reported both as absolute values and as a percent of final body weight.

Compounds of the current invention may be tested for thyroid-hormone mediated remyelination according to the following protocol.

Eight week old, male and female iCKO-Myrf mice are treated with 100 μL (20 mg/mL) tamoxifen i.p. daily for 5 days to induce oligodendrocyte depletion through deletion of Myrf from the mature oligodendrocytes (Koenning et al. 2012 J. Neuroscience). Test compounds are formulated into the food or formulated in 1% NMP/1% Solutol and dosed PO, SC or IP starting at week 2, 5 or 12 after tamoxifen induction. Dosing frequency may be daily (QD), every other day (Q2D), three times a week (QIW) or weekly (QW). The functional impact of central demyelination is measured by subjecting the mice to an accelerating rotorod technique where the time at which the mice fall off of a rotating rod is indicative of their neuromuscular function. Mice are subjected to the rotorod protocol weekly, every other week or at specific times during the study. Loss of myelination is associated with decreased time such that a nadir in ability occurs around 12 weeks after tamoxifen treatment. Partial recovery occurs from 12-24 weeks. Mice are sacrificed at 24 weeks after tamoxifen induction and brain and spinal cord tissues examined for remyelination using histologic analysis.

Compounds of the current invention may be tested for thyroid-hormone mediated inhibition of fibrosis according to the following protocol.

Adult male, C57Bl/6 mice are induced with pulmonary fibrosis through a single oropharangeal (OP) administration of 1.5-2 U/kg of bleomycin. Test compounds are formulated in 1% NMP/1% Solutol and dosed PO, SC or IP, QD starting at day −1 (prophylactic) or Day 7 (therapeutic) after bleomycin administration. On Day 21, mice are anesthetized and blood drawn via cardiac puncture. Lungs are excised and weighed, subjected broncheoalveolar lavage, inflated and fixed for histologic analysis. Lung samples are embedded in paraffin and stained with hematoxylin and eosin and Masson's tri chrome stain. A pathologist evaluates degree of fibrosis using the Ashcroft's score to quantify fibrosis. A minimum of 10 sites per lung are assessed and an average score reported for each lung.

Tissue Distribution Studies

For tissue concentration studies in male C57Bl/6 mice, test compounds are formulated as NMP/solutol/PBS solution, at a concentration of 0.05 mg/mL and dosed at 2 mL/kg with the targeted dose of 0.100 mg/kg via SC injection or oral dosing. Plasma, brain, liver, lung, kidney, heart and other selected tissue samples are collected at 0.5, 2, 8 and 24 hr (for AUC determination) or 1 hr (single time point) post-dose with three animals per time point. Tissue homogenates and plasma concentrations of test compounds are determined using LC-MS/MS with lower limits of quantitation of 0.0200 ng/mL or 0.100 ng/g. The pharmacokinetic parameters are determined by non-compartmental methods using WinNonlin.

Figure 2:
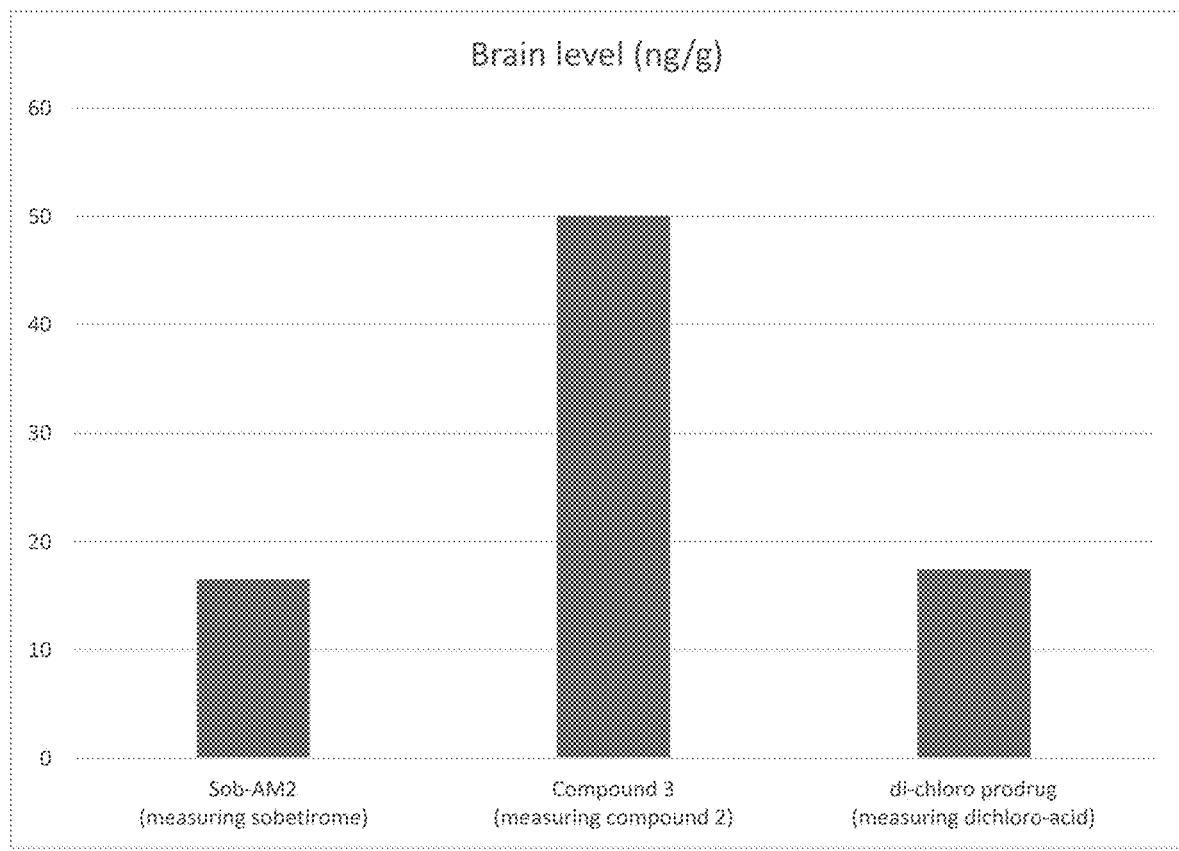
FIG. 2 depicts the concentration of select compounds in brain tissue.

FIG. 2 depicts brain levels of Compound 2 recorded 1 hr after SC dosing (0.1 mg/kg) of the corresponding prodrug Compound 3. Compound 3 ($X^1$=Me, $X^2$=Cl, $R^1$=NHMe), a brain-targeted prodrug of Compound 2 ($X^1$=Me, $X^2$=Cl, $R^1$=OH), unexpectedly shows a dramatic increase in brain concentration of the parent acid when compared to a symmetrical version with two chlorine atoms ($X^1$=$X^2$=Cl, $R^1$=NHMe, "dichloro-prodrug") or with two methyl groups ($X^1$=$X^2$=Me, $R^1$=NHMe, "Sob-AM2"). As indicated in FIG. 2, in each case levels of the parent acid are measured. As a consequence, Compound 3 is expected to have superior potency in targeting indications for which brain drug levels are predictive of activity.

Gene Activation

Adult male Sprague-Dawley rats or C57BL/6 mice are dosed orally with test compounds at up to 3 dose levels (e.g. 1×, 3× and 10× higher than the $ED_{50}$ values obtained in the cholesterol lowering studies described above). At predefined times, 4, 8 or 24 hrs after test compound administration, rodents are anesthetized and blood is drawn for plasma samples to measure drug concentrations. Samples of multiple organs including, but not limited to, liver, brain, kidney, heart, lung, skeletal muscle, pituitary and testes, are harvested and processed for RNA analysis. Samples are analyzed either by RNA-Seq after RNA isolation or by targeted gene analysis using an appropriate platform such as Quantigene™ which does not require RNA isolation. Multiple genes are used to represent a T3-mediated gene signature in each tissue; different genes are used for each tissue and all are normalized to multiple housekeeping genes that account for any variability in overall RNA quality.

Conversion Studies

Amides of Formula II may be converted to active agonist acids of Formula IV through the action of amidases such as FAAH. Similarly, esters of Formula III may be converted to active agonist acids of Formula IV through the action of various esterases. This in vivo conversion can be demonstrated through pharmacokinetics studies which measure the level of test compounds as described below:

The pharmacokinetics of test compounds are evaluated following IV, PO or SC administration to fasted male Sprague-Dawley rats (N=3/route/dose). Test compounds are dosed as clear solutions in NMP/solutol/PBS, at a concentration of 0.1 mg/mL as a single dose via IV injection (0.1 mg/kg) or orally (1 mg/kg) or subcutaneous injection (SC, 0.1 mg/kg). Blood samples are collected into $K_2$EDTA tubes at pre-dose, 0.083, 0.25, 0.5, 1, 2, 4, 8 and 24 hours post-dose administration. Plasma concentrations of test compounds are determined using LC-MS/MS with a lower limit of quantitation of 0.0200 ng/mL. The pharmacokinetic parameters are determined by non-compartmental methods using WinNonlin.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. In addition, the terms used in the following claims should not be construed as limited to the specific embodiments disclosed in the specification, but should be construed to include all possible embodiments along with the full scope of equivalents to which such claims are entitled.

This application claims the benefit of priority to PCT Application No. PCT/CN2018/120634, filed Dec. 12, 2018, and U.S. Provisional Application No. 62/907,455, filed Sep. 27, 2019, which applications are hereby incorporated by reference in their entirety.

The invention claimed is:

1. A compound having the structure of Formula (II):

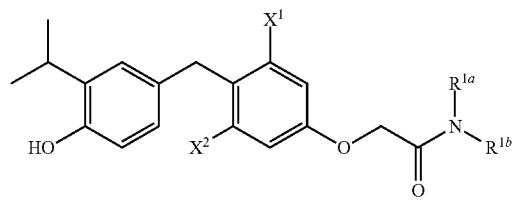

(II)

or a pharmaceutically acceptable isomer, racemate, hydrate, solvate, isotope, or salt thereof, wherein:
$X^1$ is lower alkyl;
$X^2$ is halo;
$R^{1a}$ and $R^{1b}$ are each, independently, H, $-OR^a$, $-NR^aR^b$, lower alkyl, lower alkenyl, lower alkynyl, carbocycle, carbocyclealkyl, heterocycle, or heterocyclealkyl, wherein $R^a$ and $R^b$ are each, independently, H or lower alkyl; and
wherein $R^{1a}$, $R^{1b}$, $R^a$, and $R^b$ are each, independently, optionally substituted with one or more halo, cyano, $-OR'$, $-NR'R''$, $-S(O)_2R'$ or $-S(O)_2OR'$, wherein $R'$ and $R''$ are each, independently, H or lower alkyl.

2. The compound of claim 1, or a pharmaceutically acceptable isomer, racemate, hydrate, solvate, isotope, or salt thereof, wherein $R^{1a}$ is H or lower alkyl.

3. The compound of claim 2, or a pharmaceutically acceptable isomer, racemate, hydrate, solvate, isotope, or salt thereof, wherein $R^{1a}$ is methyl.

4. The compound of claim 2, or a pharmaceutically acceptable isomer, racemate, hydrate, solvate, isotope, or salt thereof, wherein $R^{1b}$ is H or lower alkyl.

5. The compound of claim 4, or a pharmaceutically acceptable isomer, racemate, hydrate, solvate, isotope, or salt thereof, wherein $R^{1b}$ is H.

6. The compound of claim 1, or a pharmaceutically acceptable isomer, racemate, hydrate, solvate, isotope, or salt thereof, wherein $X^1$ is $-CH_3$.

7. The compound of claim 1, or a pharmaceutically acceptable isomer, racemate, hydrate, solvate, isotope, or salt thereof, wherein $X^2$ is Cl.

8. The compound of claim 1, or a pharmaceutically acceptable isomer, racemate, hydrate, solvate, isotope, or salt thereof, wherein $X^2$ is Br.

9. The compound of claim 1, or a pharmaceutically acceptable isomer, racemate, hydrate, solvate, isotope, or salt thereof, having the following structure:

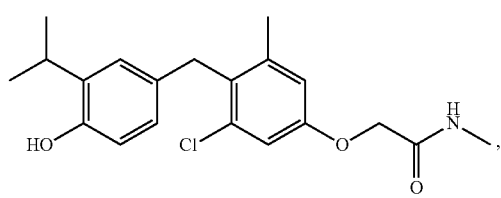

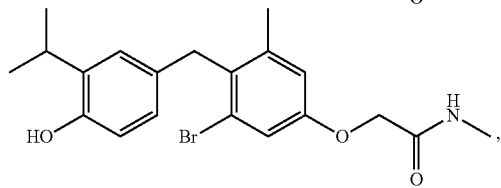

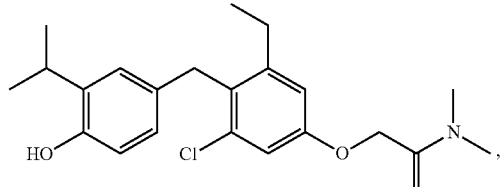

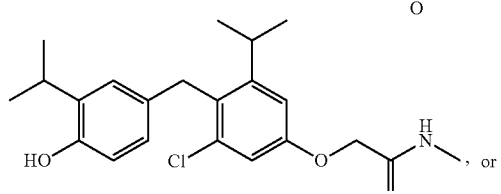

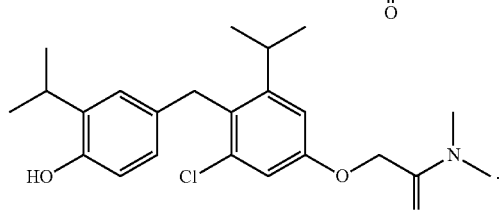

10. A pharmaceutical composition comprising a compound of claim 1, or a pharmaceutically acceptable isomer, racemate, hydrate, solvate, isotope, or salt thereof, and a pharmaceutically acceptable excipient.

* * * * *

UNITED STATES PATENT AND TRADEMARK OFFICE
CERTIFICATE OF CORRECTION

| | |
|---|---|
| PATENT NO. | : 11,827,596 B2 |
| APPLICATION NO. | : 16/712815 |
| DATED | : November 28, 2023 |
| INVENTOR(S) | : Thomas von Geldern et al. |

It is certified that error appears in the above-identified patent and that said Letters Patent is hereby corrected as shown below:

In the Claims

Column 70, Line 3:
In Claim 6, replace "X' is" with --$X^1$ is--

Signed and Sealed this
Twenty-third Day of January, 2024

*Katherine Kelly Vidal*

Katherine Kelly Vidal
*Director of the United States Patent and Trademark Office*